United States Patent
Kikuchi et al.

(10) Patent No.: US 6,242,514 B1
(45) Date of Patent: *Jun. 5, 2001

(54) PENTAVALENT PHOSPHORUS COMPOUND, PRODUCTION AND USE THEREOF

(75) Inventors: Taketoshi Kikuchi, Toyonaka; Naoki Inui, Yamatokoriyama; Kanako Fukuda, Sakai; Takashi Sanada, Ichihara, all of (JP)

(73) Assignee: Sumitomo Chemical Company, Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/979,106

(22) Filed: Nov. 26, 1997

(30) Foreign Application Priority Data

Nov. 28, 1996 (JP) .................................................... 8-318281
Jun. 27, 1997 (JP) .................................................... 9-171858

(51) Int. Cl.$^7$ ............................. C07F 9/6574; C08K 5/523
(52) U.S. Cl. ............................. 524/117; 524/119; 558/82; 558/86
(58) Field of Search .................... 558/82, 86; 524/117

(56) References Cited

U.S. PATENT DOCUMENTS

| | | | | |
|---|---|---|---|---|
| 2,661,366 | * | 12/1953 | Gamrath et al. ................. | 558/86 |
| 4,171,298 | | 10/1979 | Minagawa et al. . | |
| 4,185,006 | * | 1/1980 | Rasberger et al. ............ | 558/82 X |
| 4,198,492 | * | 4/1980 | Izawa et al. .................... | 525/134 |
| 4,298,520 | | 11/1981 | Minagawa et al. . | |
| 4,427,813 | * | 1/1984 | McEwen et al. ................ | 524/119 |
| 4,439,564 | | 3/1984 | Chasar ........................ | 524/117 X |
| 5,072,014 | * | 12/1991 | Flury ............................... | 558/86 |
| 5,298,498 | * | 3/1994 | Johnson et al. .............. | 558/82 X |
| 5,648,370 | * | 7/1997 | Bonnert et al. ................. | 514/367 |

OTHER PUBLICATIONS

STN International, CAPLUS Database, Chemical Abstracts Service, (Columbus, Ohio), No. 1976:134988; Wadsworth, W.S. et al. J. Org. Chem. 41(7): 1264–6 (1976).*
STN International, CAPLUS Database, Chemical Abstracts Service, (Columbus, Ohio), No. 1992:565620; Wu, S.Y. et al. Chem. Res. Toxicol. 5(5): 680–4 (1992).*
STN International, CAPLUS Database, Chemical Abstracts Service, (Columbus, Ohio), No. 1992:49355; Namita et al. JP 03–204888. Sep. 6, 1992.*
Database CAPLUS on STN®, Chemical Abstracts Service, (Columbus, Ohio), Accession No. 1994:270546: Reddy, C.D. et al. Phosphorus, Sulfur Silicon Relat. Elem. (1993), 81(1–4), 61–71, abstract, 1994.*
Database CAPLUS on STN®, Chemical Abstracts Service, (Columbus, Ohio), Accession No. 1977:567295; Bui Cong, C. et al. Tetrahedron Lett. (1977), (18), 1587–90, abstract, 1977.*

* cited by examiner

Primary Examiner—Michael G. Ambrose
(74) Attorney, Agent, or Firm—Pillsbury Winthrop LLP

(57) ABSTRACT

A pentavalent phosphorous compound represented by the formula (I):

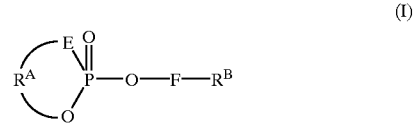

wherein $R^A$ forms a cyclic group together with E, O and P, E represents a direct bond or oxygen atom, F represents a connecting group, and $R^B$ represents a phenyl group which may be optionally substituted; and the pentavalent phosphorous compound is useful as a stabilizer for an organic material.

9 Claims, No Drawings

PENTAVALENT PHOSPHORUS COMPOUND, PRODUCTION AND USE THEREOF

The present invention relates to a novel pentavalent phosphorus-containing compound, a method for producing the same and use thereof.

When organic materials such as a thermoplastic resin, thermosetting resin, natural or synthetic rubber, mineral oil, lubricating oil, adhesive, paint and the like are produced, processed or used, they are tend to be degraded by the action of heat, oxygen and the like. Such degradation causes decrease in physical strength, change of flowability, coloration, decrease in surface physical property and the like of the organic materials, and lowers market value thereof remarkably. It is conventionally known to include various phenolic antioxidants, phosphorus antloxidants and the like in an organic material in order to solve such problems as heat degradation and oxygen degradation and to stabilize the organic material.

For example, as the phosphorus antioxidant, pentavalent phosphorus compounds such as 3,5-di-t-butyl-4-hydroxybenzylphosphonate diethylester are known. However, these known phosphorus antioxidants are still insufficient in stabilization effect against heat degradation and oxygen degradation.

The present inventors have produced various phosphorus compounds and intensively studied about them, and as a result, found that a specific phosphorus compound such as a cyclic pentavalent phosphorus compound exhibits excellent stabilization effect. The present invention was thus completed.

The present invention provides a pentavalent phosphorus compound represented by the formula (I):

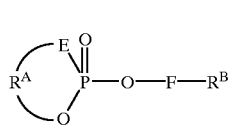

(I)

wherein $R^A$ forms a cyclic group together with E, O and P, E represents a direct bond or oxygen atom, F represents a connecting group, and $R^B$ represents a phenyl group which may be optionally substituted.

The present invention also provides a method for producing the same, and use thereof.

In the pentavalent phosphorus compound of formula (I), $R^A$ forms a cyclic group together with E, O and P. Examples of $R^A$ include a bisphenylene group having a total carbon atom number of about 12 to 80, which may be optionally substituted, a phenylene group having a total carbon atom number of about 6 to 30, which may be optionally substituted, or an alkylene group having a total carbon atom number of about 3 to 60, which may be optionally substituted.

Typical examples of the bisphenylene group as $R^A$ include a biphenylene group, an alkylenebisphenylene group or a thiobisphenylene group, represented by the formula (II):

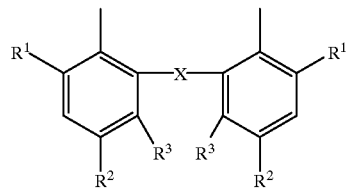

(II)

wherein $R^1$ and $R^2$ each independently represents a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, $R^3$ represents a hydrogen atom or alkyl group having 1 to 8 carbon atoms, X represents a direct bond, sulfur atom, unsubstituted methylene group or methylene group substituted with an alkyl having 1 to 8 carbon atoms or a cycloalkyl having 5 to 8 carbon atoms.

Typical examples of the phenylene group as $R^A$ include o-phenylene group represented by the formula (III):

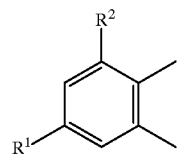

(III)

wherein $R^1$ and $R^2$ are as defined above.

In the formulae (II) and (III), substituents $R^1$ and $R^2$ each independently represent a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group. In the formula (II), substituent $R^3$ represents a hydrogen atom or alkyl group having 1 to 8 carbon atoms.

Typical examples of the alkyl group having I to 8 carbon atoms, as $R^1$, $R^2$ or $R^3$, include methyl, ethyl, n-propyl, i-propyl, n-butyl, i-butyl, sec-butyl, t-butyl, t-pentyl, i-octyl, t-octyl and 2-ethylhexyl.

Typical examples of the cycloalkyl group having 5 to 8 carbon atoms, as $R^1$ or $R^2$, include cyclo-entyl, cyclohexyl, cycloheptyl and cyclooctyl.

Typical examples of the alkylcycloalkyl group having 6 to 12 carbon atoms, as $R^1$ or $R^2$, include 1-methylcyclopentyl, 1-methylcyclohexyl and 1-methyl-4-i-propylcyclohexyl.

Typical examples of the aralkl group having 7 to 12 carbon atoms, as $R^1$ or $R^2$, include benzyl, a-methylbenzyl and α,α-dimethylbenzyl.

$R^1$ is preferably t-alkyl group such as t-butyl, t-pentyl, t-octyl and 1-methylcyclohexyl. $R^2$ is preferably alkyl group having 1 to 5 carbon atoms such as methyl, ethyl, n-propyl, i-propyl, n-butyl, i-butyl, sec-butyl, t-butyl and t-pentyl, and particularly preferably t-butyl. $R^3$ is preferably a hydrogen atom or alkyl group having 1 to 5 carbon atoms, and particularly preferably a hydrogen atom or methyl group.

The substituent X represents a direct bond, sulfur atom, unsubstituted methylene group or methylene group substituted with alkyl having 1 to 8 carbon atoms or cycloalkyl having 5 to 8 carbon atoms. Typical examples of said alkyl group having 1 to 8 carbon atoms, as the substituent on the methylene group as X, include methyl, ethyl, n-propyl, i-propyl, n-butyl, i-butyl, sec-butyl, t-butyl, t-pentyl, i-octyl, t-octyl and 2-ethylhexyl. Typical examples of said cycloalkyl group having 5 to 8 carbon atoms, as the substituent on the methylene group as X, include cyclopentyl, cyclohexyl, cycloheptyl and cyclooctyl.

X is preferably a direct bond, unsubstituted methylene group or methylene group substituted with methyl group.

Typical examples of the alkylene group as $R^A$ include propylene group represented by the formulae (IV):

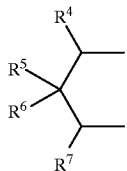
(IV)

wherein $R^4$, $R^5$, $R^6$ and $R^7$ each independently represent a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, and ethylene group represented by the formulae (V):

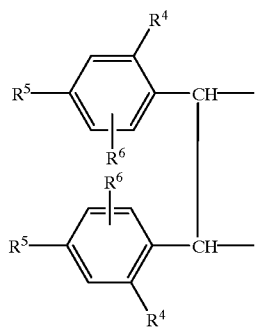
(V)

wherein $R^4$, $R^5$ and $R^6$ are as defined above.

Typical examples of the alkyl group having 1 to 8 carbon atoms, as $R^4$, $R^5$, $R^6$ or $R^7$, include methyl, ethyl, n-propyl, i-propyl, n-butyl, i-butyl, sec-butyl, t-butyl, t-pentyl, i-octyl, t-octyl and 2-ethylhexyl.

Typical examples of the cycloalkyl group having 5 to 8 carbon atoms, as $R^4$, $R^5$, $R^6$ or $R^7$, include cyclopentyl, cyclohexyl, cycloheptyl and cyclooctyl. Typical examples of the alkylcycloalkyl group having 6 to 12 carbon atoms, as $R^4$, $R^5$, $R^6$ or $R^7$, include 1-methylcyclopentyl, 1-methylcyclohexyl and 1-methyl-4-i-propylcyclohexyl. Typical examples of the aralkyl group having 7 to 12 carbon atoms, as $R^4$, $R^5$, $R^6$ or $R^7$, include benzyl, α-methylbenzyl and α,α-dimethylbenzyl.

$R^4$, $R^5$, $R^6$ and $R^7$ are preferably a hydrogen atom or alkyl group having 1 to 8 carbon atoms, and more preferably a hydrogen atom or methyl group.

The mark E in the formula (I) represents a direct bond or oxygen atom, and preferably an oxygen atom.

The mark F represents a connecting group. Examples of such connecting group as F include a direct bond and a divalent connecting group having about 1 to 20 carbon atoms in total optionally having a hetero atom. Specific example of the divalent connecting group include those represented by the following formulae (VI) (VII), (VIII), (IX), (X), (XI) or (XII):

$*$—A—  (VI)

$*$—C(O)—A—  (VII)

$*$—B—O—A—  (VIII)

$*$—B—O—C(O)—A—  (IX)

$*$—D—C(O)—O—A—  (X)

$*$—G—N($R^8$)—A—  (XI)

$*$—G—N($R^8$)—C(O)—A—  (XII)

wherein $*$— represents a bond to the oxygen atom, A represents a direct bond or an alkylene group having 1 to 8 carbon atoms, B represents a divalent alcohol residue, D represents an alkylene group having 1 to 8 carbon atoms, G represents an alkylene group having 2 to 8 carbon atoms, and $R^8$ represents a hydrogen atom, an alkyl group having 1 to 8 carbon atoms or a group represented by the formula (XIII)

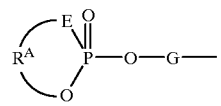
(XIII)

wherein $R^A$, E and G are as defined above.

Typical examples of said alkylene group having 1 to 8 carbon atoms, as A or D, include straight-chain alkylene such as methylene, ethylene, propylene, butylene, pentamethylene, hexamethylene and octamethylene; branched alkylenes such as 1-methylethylene, dimethylmethylene and 2,2-dimethyl-1,3-propylene.

The divalent alcohol residue, as B, means a residue obtained by removing two hydroxyl groups from a divalent alcohol. Representative examples thereof include residues of alkylene diols such as ethylene glycol, 1,2-propane diol, 1,3-propane diol, 1,2-butane diol, 1,3-butane diol, 1,4-butane diol, 2,3-butane diol, 2-methyl-1,3-propane diol, 1,2-pentane diol, 1,5-pentane diol, 2,4-pentane diol, neopentyl glycol, 1,2-hexane diol, 1,5-hexane diol, 1,6-hexane diol, 2,5-hexane diol, 2-methyl-2,4-pentane diol, 2-methyl-1,5-pentane diol, 3,3-dimethylbutane diol, 2,3-dimethyl-2,3-butane diol, 2-ethyl-2-methyl-1,3-propanol, 2,2-diethyl-1,3-propane diol, 2,4-dimethyl-2,4-pentane diol, 1,2-octane diol, 1,8-octane diol, 2,5-dimethyl-2,5-hexane diol, 2-ethyl-1,3-hexane diol, 2,2,4-trimethyl-1,3-pentane diol, 1,9-nonane diol, 2-butyl-2-ethyl-1,3-propane diol, 1,2-decane diol, 1,10-decane diol, 1,12-dodecane diol, 1,2-tetradecane diol, 1,14-tetradecane diol, 1,2-hexadecane diol and 1,16-hexadecane diol; residues of diols having a double bond such as 2-butene-1,4-diol, 2-methylene-1,3-dropane diol, 5-hexene-1,2-diol and 7-octane-1,2-diol; residues of cyclic diols such as 1,2-cyclopentane diol, 1,3-cyclopentane diol, 1,2-cyclohexane diol, 1,3-cyclohexane diol, 1,4-cyclohexan diol 1,2-cycloocta diol, 1,4-cyclooctane diol, 1,5-cyclooctane diol, p-pentane-3,8-diol and 4,4'-isopropylidenedicyclohexanol; and diols having a hetero atom such as diethylene glycol, triethylene glycol, 3,9-bis (1,1-dimethyl-2-hydroxyethyl)-2,4,8,10-tetraoxaspiro[5,5] undecane, neopentyl glycol hydroxypivalate, 2,2'-thiodiethanol, 2-methylthio-1,2 -propane diol and diethanolamine.

The representative examples of the alkylene group having 2 to 8 carbon atoms, as G, include straight-chain alkylenes such as ethylene, propylene, butylene, pentamethylene, hexamethylene and octamethylene; and branched alkylenes such as 1-methylethylene and 2,2-dimethyl-1,3-propylene.

Typical examples of the alkyl group having 1 to 8 carbon atoms, as $R^8$, include methyl, ethyl, n-propyl, i-propyl, n-butyl, i-butyl, sec-butyl, t-butyl, t-pentyl, i-octyl, t-octyl and 2-ethylhexyl.

When the connecting group F is represented by the formula (VI), the mark A is preferably a direct bond or an alkylene group having 2 to 8 carbon atoms, and particularly preferably a direct bond or propylene.

When the connecting group F is represented by the formula (VII), the mark A is preferably a direct bond or ethylene.

When the connecting group F is represented by the formula (VIII), the mark A is preferably methylene and the mark B is preferably ethylene or propylene.

Further, when the connecting group F is represented by the formula (IX), the mark A is preferably a direct bond, ethylene or dimethylmethylene and the mark B is preferably an ethylene glycol residue or 1,2-propane diol residue.

Further when the connecting group F is represented by the formula (X), the mark A is preferably a direct bond or methylene and the mark D is preferably methylene.

Further when the connecting group F is represented by the formula (XI), the mark A is preferably methylene or ethylene, the mark G is preferably ethylene or propylene, and $R^8$ is preferably hydrogen, methyl, ethyl or a compound represented by the formula (XIII).

Further when the connecting group F is represented by the formula (XII), the mark A is preferably a direct bond or ethylene, the mark G is preferably ethylene or propylene, and the $R^8$ is preferably hydrogen, methyl, ethyl or compound represented by the formula (XIII).

The group $R^B$ in the formula (I) represents a phenyl group optionally having a substituent, and the total number of the carbon atom are usually from 6 to 30.

Representative examples of such a phenyl group, as $R^B$, include groups represented by the formula (XIV):

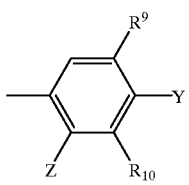

(XIV)

wherein $R^9$ and $R^{10}$ each independently represent a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, and Y and Z each independently represent a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms, phenyl group, hydroxyl group, alkoxy group having 1 to 8 carbon atoms or aralkyloxy group having 7 to 12 carbon atoms; and groups represented by the formula (XV):

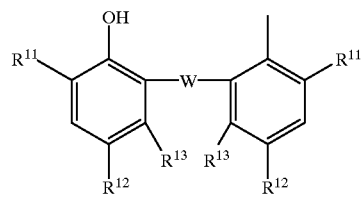

(XV)

wherein $R^{11}$ and $R^{12}$ each independently represent a hydrogen atom, alkyl group having 1 to 8 carbon atoms, cycloalkyl group having 5 to 8 carbon atoms, alkylcycloalkyl group having 6 to 12 carbon atoms, aralkyl group having 7 to 12 carbon atoms or phenyl group, and $R^{13}$ represents a hydrogen atom or alkyl group having 1 to 8 carbon atoms, W represents a direct bond, sulfur atom, unsubstituted methylene group or methylene group substituted with an alkyl group having 1 to 8 carbon atoms or cycloalkyl group having 5 to 8 carbon atoms.

Typical examples of the alkyl group having 1 to 8 carbon atoms, as $R^9$, $R^{10}$, $R^{11}$, $R^{12}$, Y, Z, $R^{13}$ or W, include methyl, ethyl, n-propyl, i-propyl, n-butyl, i-butyl, sec-butyl, t-butyl, t-pentyl, i-octyl, t-octyl and 2-ethylhexyl.

Typical examples of the cycloalkyl group having 5 to 8 carbon atoms, as $R^9$, $R^{10}$, $R^{11}$, $R^{12}$, Y, Z or W, include cyclopentyl, cyclohexyl, cycloheptyl and cyclooctyl.

Typical examples of the alkylcycloalkyl group having 6 to 12 carbon atoms, as $R^9$, $R^{10}$, $R^{11}$, $R^{12}$, Y or Z, include 1-methylcyclopentyl, 1-methylcyclohexyl and 1-methyl-4-i-propylcyclohexyl.

Typical examples of the aralkyl group having 7 to 12 carbon atoms, as $R^9$, $R^{10}$, $R^{11}$, $R^{12}$, Y or Z, include benzyl, α-methylbenzyl and α,α-dimethylbenzyl.

Examples of the alkoxy group having 1 to 8 carbon atoms, as Y or Z, include alkoxy groups in which the alkyl moiety is methyl, ethyl, n-propyl, i-propyl, n-butyl, i-butyl, sec-butyl, t-butyl, t-pentyl, i-octyl, t-octyl or 2-ethylhexyl.

Examples of the aralkyloxy group having 7 to 12 carbon atoms, as Y or Z, include aralkyloxy groups in which the aralkyl moiety is benzyl, α-methylbenzyl or α,α-dimethylbenzyl.

$R^9$ is preferably methyl, t-butyl, t-pentyl or t-octyl. $R^{10}$ is preferably a hydrogen atom, methyl, t-butyl, t-pentyl or t-octyl.

It is preferred that one of Y and Z is a hydroxyl group, alkoxy group having 1 to 8 carbon atoms or aralkyloxy group having 7 to 12 carbon atoms, and other is a hydrogen atom or alkyl group having 1 to 8 carbon atoms. It is more preferred that either of them is a hydroxyl group or methoxy group.

$R^{11}$ is preferably t-alkyl group such as t-butyl, t-pentyl, t-octyl or 1-methylcyclohexyl. $R^{12}$ is preferably an alkyl group having 1 to 5 carbon atoms such as methyl, ethyl, n-propyl, i-propyl, n-butyl, i-butyl, sec-butyl, t-butyl or t-pentyl, and particularly preferably t-butyl. $R^{13}$ is preferably a hydrogen atom or alkyl group having 1 to 5 carbon atoms, and particularly preferably a hydrogen atom or methyl group.

W is preferably a direct bond, methylene group or methylene group substituted with a methyl group.

When $R^B$ is a group represented by the formula (XV), the connecting group F is preferably a direct bond.

The pentavalent phosphorus compound of formula (I) can be produced by reacting a halogen phosphate represented by the formula (XVI)

$$\begin{array}{c} \phantom{R^A}\overset{E}{\diagup}\overset{O}{\underset{\diagdown}{\overset{\|}{P}}}\!-\!V \\ R^A \phantom{\overset{E}{\diagup}} \\ \phantom{R^A}\diagdown_{O}\diagup \end{array} \quad (XVI)$$

wherein $R^A$ and E are as define above, and V represents a halogen atom, with a hydroxy compound represented by the formula (XVII)

$$HO-F-R^B \quad (XVII)$$

wherein, F an $R^B$ are as define above; or by oxidizing a corresponding trivalent phosphorus compound.

The reaction of halogenooxy phosphate of formula (XVI) with the hydroxy compound of formula (XVII) can be accelerated by a de-hydrogen halide agent such as amines, pyridines, pyrrolidines or amides, or a hydroxide of alkaline metal or alkaline earth metal.

Said amines may be any of primary, secondary or tertiary amines. Examples thereor include t-butylamine, t-pentylamine, t-hexylamine, t-octylamine, di-t-butylamine, di-t-pentylamine, di-t-hexylamine, di-t-octylamine, trimethylamine, triethylamine, N,N-dimethylaniline and N,N-diethylaniline. Among them, triethylamine is preferred.

Examples of the pyridines include pyridine and picoline, and pyridine is preferred. Examples of the pyrrolidines include 1-methyl-2-ovrrolidine.

Examples of the amides include N,N-dimethylformamide and N,N-dimethylacetoamide, and N,N-dimethylformamide is preferably used.

Examples of the hydroxides of alkaline metal or alkaline earth metal include sodium hydroxide and potassium hydroxide, and Preferably sodium hydroxide.

The reaction is usually conducted in an organic solvent. The organic solvent is not particularly restricted as long as it does not interfere the reaction. Examples thereof include aromatic hydrocarbons, aliphatic hydrocarbons, oxygen-containing hydrocarbons and halogenated hydrocarbons.

Examples of the aromatic hydrocarbons include benzene, toluene, xylene and ethylbenzen, examples of the aliphatic hydrocarbons include n-hexane, n-heptane and n-octane, examples of the oxygen-containing hydrocarbons include diethyl ether, dibutyl ether, tetrahydrofuran and 1,4-dioxane, and examples of the halogenated hydrocarbons include chloroform, carbon tetrachloride, monochlorobenzene, dichloromethane, 1,2-dichloroethane and dichlorobenzene.

Among them, toluene, xylene, n-hexane, n-heptane, diethyl ether, tetrahydrofuran, 1,4-dioxane, chloroform and dichloromethane are preferably used.

Usually, the halogeno phosphate (XVI) is reacted with the hydroxy compound (XVII) in the presence of a de-hydrogen halide agent. When the de-hydrogen halide agent is used in the reaction, the hydroxy compound (XVII) is used in an amount of usually from 0.9 to 1.1-fold by mol, and preferably from 0.95 to 1.05-fold by mol based on the halogenooxy phosphate (XVI).

When the de-hydrogen halide agent is used, the agent is used in an amount preferably from 1 to 2-fold by mol, and more preferably from 1 to 1.3-fold by mol based on the halogenooxyphosphate (XVI). There action is usually carried out at a temperature from 0 to 200° C.

When the de-hydrogen halide agent is used, after the reaction is completed, the hydrogen halide salt of the de-hydrogen halide agent produced in the reaction is removed, then, the solvent is removed, followed by conducting a suitable pre-treatment such as crystallization and column chromatography, to obtain the pentavalent phosphorus compound of formula (I).

The mark V in the formula (XVI)represents a halogen atom such as fluorine, chlorine and bromine.

The halogenooxy phosphate of formula (XVI) in which E is an oxygen atom can be produced, for example, by reacting an phosphorus oxyhalide with corresponding bisphenols when $R^A$ is a bisophenylene group of formula (II), with corresponding catechols when $R^A$ is a o-phenylene group of formula (III) or with corresponding diols when $R^A$ is an alkylene group of formula (IV) or (V) according to methods described in U.S. Pat. No. 5,245,069 Nature, 157, 133 (1946) etc.

A halogeno phosphate (XVI) in which E is a direct bond can be produced, for example, by reacting 2-phenylphenols with a phosphorus oxyhalide such as phosphorus oxychloride by using a Friedel Crafts catalyst such as zinc chloride and aluminum chloride according to a method described in Phosphorus and Sulfur 31. 71 (9187).

Examples of the bisphenol used for the production of the halogenooxy phosphate of formula (XVI) include 2,2'-methylenebis(4-methyl-6-t-butylphenol), 2,2'-methylenebis(4-ethyl-6-t-butylphenol), 2,2'-methylenebis(4-n-propyl-6-t-butylphnenol), 2,2'-methylenebis(4-i-prouyl-6-t-butylphenol), 2,2'-methylenebis-(4-n-butyl-6-t-butylphenol, 2,2'-methylenebis(4-i-butyl-6-t-butylphenol), 2,2'-methylenebis(4,6-di-t-butylphenol), 2,2'-methylenebis(4-t-pentyl-6-t-butylphenol), 2,2'-methylenebis(4-nonyl-6-t-butylphenol), 2,2'-methylenebis(4-t-octyl-6-t-butylphenol), 2,21'-methylenebis(4-methyl-6-t-pentylphenol), 2,2'-methylenebis(4-methyl-6-cyclohexylphenol) 2,21'-methylenebis[4-methyl-6-(α-methylcyclohexyl)phenol)], 2,2'-methylenebis(4-methyl-6-t-nonylphenol), 2,2'-methylenebis(4-methyl-6-t-octylphenol), 2,2'-methylenebis(4,6-di-t-pentylphenol), 2,2'-methylenebis[4-nonyl-6-(α-methylbenzyl)phenol], 2,2'-methylenebis[4-nonyl-6-(α,α-dimethylbenzyl)phenol], 2,2'-ethylidenebis(4-methyl-6-butylphenol), 2,2'-ethylidenebis(4-ethyl-6-t-butylphenol), 2,2'-ethylidenebis(4-n-propyl-6-t-butylphenol), 2,2'-ethylidenebis(4-i-propyl-6-t-butylphenol), 2,2'-ethylidenebis(4-n-butyl-6-t-butylphenol), 2,2'-ethylidenebis(4-i-butyl-6-t-butylphenol), 2,2'-ethylidenebis(4,6-di-t-butylphenol), 2,2'-ethylidenebis(4-t-pentyl-6-t-butylphenol), 2,2'-ethylidenebis(4-nonyl-6-t-butylphenol), 2,2'-ethylidenebis(4-t-octyl-6-t-butylphenol), 2,2'-ethylidenebis(4-methyl-6-t-pentylphenol), 2,2'-ethylidenebis(4-methyl-6-cyclohexylphenol), 2,2'-ethylidenebis[4-methyl-6-(α-methylcyclohexyl)phenol)], 2,2'-ethylidenebis(4-methyl-6-nonylphenol), 2,2'-ethylidenebis(4-methyl-6-t-octylphenol), 2,2'-ethylidenebis(4,6-di-t-pentylphenol), 2,2'-ethylidenebis[4-nonyl-6-(α-methylbenzyl)phenol], 2,2'-ethylidenebis[4-nonyl-6-(α,α-dimethylbenzyl)phenol], 2,2'-propylidenebis(4-methyl-6-t-butylphenol), 2,2'-propylidenebis(4-ethyl-6-t-butylphenol), 2,2'-propylidenebis(4-n-propyl-6-t-butylphenol), 2,2'-propylidenebis(4-i-propyl-6-t-butylphenol), 2,2'-propylidenebis(4-n-butyl-6-t-butylphenol), 2,2'-propylidenebis(4-i-butyl-6-t-butylphenol), 2,2'-propylidenebis(4,6-di-t-butylphenol), 2,2'-propylidenebis(4-t-pentyl-6-t-butylphenol), 2,2'-propylidenebis(4-nonyl-6-t-butylphenol), 2,2'-propylidenebis(4-t-octyl-6-t-butylphenol), 2,2'-propylidenebis(4-methyl-6-t-pentylphenol), 2,2'-propylidenebis(4-methyl-6-cyclohexylphenol), 2,2'-propylidenebis[4-methyl-6-(α- methylcyclohexyl)phenol)], 2,2'-propylidenebis(4-methyl-6-nonylphenol), 2,2'-propylidenebis(4-methyl-6-t-octylphenol), 2,2'-propylidenebis(4,6-di-t-pentylphenol), 2,2'-propylidenebis[4-nonyl-6-(α-methylbenzyl)phenol], 2,2'-propylidenebis[4-nonyl-6-(α,α-dimethylbenzyl) phenol], 2,2'-butylidenebis(4-methyl-6-t-butylphenol), 2,2'-butylidenebis(4-ethyl-6-t-butylphenol), 2,2'-butylidenebis(4,6-di-t-butylphenol), 2,2'-butylidenebis(4-methyl-6-cyclohexylphenol), 2,2'-butylidenebis[4-methyl-6-(α-methylcyclohexyl)phenol)], 2,2'-butylidenebis(4,6-di-t-pentylphenol), 2,2'-i-butylidenebis(4-methyl-6-t-butylphenol), 2,2'-i-butylidenebis(4-ethyl-6-t-butylphenol), 2,2'-i-butylidenebis(4,6-di-t-butylphenol), 2,2'-i-butylidenebis(4-methyl-6-cyclohexylpnenol), 2,2'-i-butylidenebis[4-methyl-6-(α-methylcyclohexyl)phenol)], 2,2'-i-butylidenebis(4,6-di-t-pentylphenol), 2,2'-i-pentylidenebis(4-methyl-6-t-butylphenol), 2,2'-i-pentylidenebis(4-ethyl-6-t-butylphenol), 2,2'-i-pentylidenebis(4,6-di-t-butylphenol), 2,2'-i-pentylidenebis(4-methyl-6-cyclohexylphenol), 2,2'-pentylidenebis[4-methyl-6-(α-methylcyclohexy)phenol], 2,2'-pentylidenebis(4,6-di-t-pentylphenol), biphenyl- 2,2'-diol, 3,3',5,5'-tetra-t-butylbiphenyl-2,2'-diol and 1,1'-binaphthyl-2,2'-diol.

The bisphenol can be produced by condensing an alkylphenol according to a known method described, for example, in JP-A-52-122350, U.S. Pat. No. 2,538,355 or JP-B-2-47451. An alkylphenol which are commercially available can also be used.

Examples of the above-described catechols used for the production of the halogeno phosphate of formula (XVI) include catechol, 3-methylcatechol, 3-ethylcatechol, 3-i-pronylcatechol, 3-t-butylcatechol, 3-t-octylcatechol, 3-phenylcatechol, 3-cyclohexylcatechol, 4-methylcatechol, 4-ethylcatechol, 4-i-propylcatechol, 4-t-butylcatechol, 4-t-octylcatechol, 4-phenylcatechol, 4-cyclohexylcatechol, 3,5-di-t-butylcatechol, 3,5-di-i-propylcatechol, 3,5-di-t-octylcatechol, 3-methyl-5-t-butylcatechol, 3-t-butyl-5-methylcatechol, 3-methyl-5-i-propylcatechol, 3-i-propyl-5-methylcatechol, 3-methyl-5-t-octylcatechol and 3-t-octyl-5-methylcatechol.

Examples of the above-described diols used for the production of the halogeno phosphate of formula (XVI) include propylene diol derivatives such as 1,3-propane diol, 2,2-dimethyl-1,3-propane diol, 2,2-diethyl-1,3-propane diol, 2-ethyl-2-methyl-1,3-propane diol, 2-methyl-1-propyl-1,3-propane diol, 2-butyl-2-ethyl-1,3-propane diol, 1-phenyl-1,3-propane diol, 2,2-dimethyl-1-phenyl-1,3-propane diol 2,2-diphenyl-1,3-propanediol, 2-methyl-benzyl-1,3-propane diol, 2,4-pentane-diol, 2-methyl-2,4 -pentane diol, 2,4-dimethyl-2,4-pentane diol, 2,2,4-trimethyl-1,3-pentane diol, 1,3-butane diol, 2,2-dimethyl-1,3-butane diol, 3-methyl-1,3-butane diol, 2,4-hexane diol, 2-ethyl-1,3-hexane diol, 3-methyl2,4-heptane diol, 5-ethyl-3-methyl-2,4-heptane diol, 2-butyl-1,3-octane diol, 5-ethyl-3-methyl-2,4-nonane diol and 7-ethyl-2-methyl-4,6-nonane diol, and ethylene glycol derivatives such as hydrobenzoin, 1,2-bis(2-t-butylphenyl)-1,2-ethane diol, 1,2-bis(4-t-butylphenyl)-1,2-ethane diol, 1,2-bis(2-t-butyl-4-methylphenyl)-1,2-ethane diol, 1,2-bis(2-t-butyl-6-methylphenyl)-1,2-ethane diol, 1,2-bis(2,4-di-t-butylphenyl)-1,2-ethane diol, 1,2-bis(2,6-di-t-butylphenyl)-1,2-ethane diol, 1,2-bis(2,4-di-t-pentylphenyl)-1,2-ethane diol, 1,2-bis(2,4-di-t-butyl-6-methylphenyl)-1,2-ethane diol, 1,2-bis(2,6-di-t-butyl-4-methylphenyl)-1,2-ethane diol and 1,2-bis(2,4,6-tri-t-butylphenyl)-1, 2-ethane diol.

The propylene glycol derivatives described above can be produced by condensation reaction of alkylaldehydes, for example, according to a method described in J. Am. Chem. Soc., 70, 1982 (1948). The ethylene glycol derivatives described above can be produced by reductive dimerization of corresponding aldehydes, for example, according to methods described in Chem. Lett., 1041 (1973), Bull. Soc. Chem. Fr., 2147 (1973), J. Organomet. Chem., 42, 277 (1972), Bull. Soc. Chim. Fr., 2011 (1967) or J. Org. Chem., 41, 260 (1976). If they are commercially available, they can also be used.

Examples for the hydroxide compound (XVII) in wnich the connecting group F is represented by the formula (VI) in which A is a direct bond include the bisphenols listed above as the starting material used for the production of the halogeno phosphate of formula (XVI).

Examples for the hydroxide compound (XVII) in which the connecting group F is represented by the formula (VI) in which A is an alkyene group having 1–8 carbon atoms include 2-(3-t-butyl-4-hydroxyphenyl)ethanol, 2-(3-t-pentyl-4-hydroxyphenyl)ethanol, 2-(3-t-octyl-4-hydroxyphenyl)ethanol, 2-(3-cyclohexyl-4-hydroxyphenyl) ethanol, 2-[3-(1-methylcyclohexyl)-4-hydroxyphenyl] ethanol, 2-(3-t-butyl-4-hydroxy-5-methylphenyl)ethanol, 2-(3-t-pentyl-4-hydroxy-5-methylphenyl)ethanol, 2-(3-t-octyl-4-hydroxy-5-methylphenyl)ethanol, 2-(3-cyclohexyl-4-hydroxy-5-methylphenyl)ethanol, 2-[3-(1-methylcyclohexyl)-4-hydroxy-5-methylphenyl]ethanol, 2-(3-t-butyl-4-hydroxy-5-ethylphenyl)ethanol, 2-(3-t-pentyl-4-hydroxy-5-ethylphenyl)ethanol, 2-(3-t-octyl-4-hydroxy-5-ethylphenyl)ethanol, 2-(3-cyclohexyl-4-hydroxy-5-ethylphenyl)ethanol, 2-[3-(1-methylcyclohexyl)-4-hydroxy-5-ethylphenyl]ethanol, 2-(3,5-di-t-butyl-4-hydroxyphenyl)ethanol, 2-(3-t-pentyl-4-hydroxy-5-t-butylphenyl)ethanol, 2-(3-t-octyl-4-hydroxy-5-t-butylphenyl)ethanol, 2-(3-cyclohexyl-4-hydroxy-5-t-butylphenyl)ethanol-, 2-[3-(1-methylcyclohexyl)-4-hydroxy-5-t-butylphenyl]ethanol, 2-(3-t-butyl-4-methoxyphenyl)ethanol, 2-(3-t-pentyl-4 -methoxyphenyl) ethanol, 2-(3-t-octyl-4-methoxyphenyl)ethanol, 2-(3-cyclohexyl-4-methoxyphenyl)ethanol, 2-[3-(1-methylcyclohexyl)-4-methoxyphenyl]ethanol, 2-(3-t-butyl-4-methoxy-5-methylphenyl)ethanol, 2-(3-t-pentyl-4-methoxy-5-methylphenyl)ethanol, 2-(3-t-octyl-4-methoxy-5-methylphenyl)ethanol, 2-(3-cyclohexyl-4-methoxy-5-methylphenyl)ethanol, 2-[3-(1-methylcyclohexyl)-4-methoxy-5-methylphenyl]ethanol, 2-(3-t-butyl-4-methoxy-5-ethylphenyl)ethanol, 2-(3-t-pentyl-4-methoxy-5-ethylphenyl)ethanol, 2-(3-t-octyl-4-methoxy-5-ethylphenyl) ethanol, 2-(3-cyclohexyl-4-methoxy-5-ethylphenyl)ethanol, 2[-3-(1-methylcyclohexyl)-4-methoxy-5-ethylphenyl] ethanol, 2-(3,5-di-t-butyl-4-methoxyphenyl)ethanol, 2-(3-t-pentyl-4-methoxy-5-t-butylphenyl)ethanol, 2-(3-t-octyl-4-methoxy-5-t-butylphenyl)ethanol, 2-(3-cyclohexyl-4-methoxy-5-t-butylphenyl)ethanol, 2-[3-(1-methylcyclohexyl)-4-methoxy-5-t-butylphenyl]ethanol, 3-(3-t-butyl-2-hydroxyphenyl)propanol, 3-(3-t-butyl-4-hydroxyphenyl)propanol, 3-(5-t-butyl-2-hydroxyphenyl) propanol, 3-(3-t-pentyl-4-hydroxyphenyl)propanol, 3-(3-t-octyl-4-hydroxyphenyl)propanol, 3-(3-cyclohexyl-4-hydroxyphenyl)propanol, 3-[3-(1-methylcyclohexyl)-4-hydroxyphenyl]propanol, 3-(3-t-butyl-2-hydroxy-5-methylphenyl)propanol, 3-(3-t-butyl-4-hydroxy-5-methylphenyl)propanol, 3-(5-t-butyl-2 -hydroxy-3-methylphenyl)propanol, 3-(3-t-pentyl-4-hydroxy-5-methylphenyl)propanol, 3-(3-t-octyl-4-hydroxy-5-methylphenyl)propanol, 3-(3-cyclohexyl-4-hydroxy-5-methylphenyl)propanol, 3-[3-(1-methylcyclohexyl)-4-hydroxy-5-methylphenyl]propanol, 3-(3-t-butyl-4-hydroxy- 5-ethylphenyl)propanol, 3-(3-t-pentyl-4-hydroxy-5-ethylphenyl)propanol, 3-(3-t-octyl-4-hydroxy-5-ethylphenyl)propanol, 3-(3-cyclohexyl-4-hydroxy-5-ethylphenyl)propanol, 3-[3-(1-methylcyclohexyl)-4-hydroxy-5-ethylphenyl]propanol, 3-(3,5-di-t-butyl-2-hydroxyphenyl)propanol, 3-(3,5-di-t-butyl-4-hydroxyphenyl)propanol, 3-(3-t-pentyl-4-hydroxy-5-t-butylphenyl)propanol, 3-(3-t-octyl-4-hydroxy-5-t-butylphenyl)propanol, 3-(3-cyclohexyl-4-hydroxy-5-t-buthylphenyl)propanol, 3-[3-(1-methylcyclohexyl)-4-hydroxy-5-t-buthylphenyl]propanol 3-(3-t-butyl-2-methoxyphenyl)propanol, 3-(3-t-butyl-4-methoxyphenyl)propanol, 3-(3-t-butyl-5-methoxyphenyl)propanol, 3-(3-t-pentyl-4-methoxyphenyl)propanol, 3-(3-t-octyl-4-methoxyphenyl)propanol, 3-(3-cyclohexyl-4-methoxyphenyl)propanol, 3-[3-(1-methylcyclohexyl)-4-methoxyphenyl]poropanol, 3-(3-t-butyl-2-methoxy-5-methylphenyl)propanol 3-(3-t-butyl-4-methoxy-5-methylphenyl)propanol, 3-(5-t-butyl-2-methoxy-3-methylphenyl)propanol, 3-(3-t-pentyl-4-methoxy-5-methylphenyl)propanol, 3-(3-t-octyl-4-methoxy-5-methylphenyl)propanol, 3-(3-cyclohexyl-4-methoxy-5-methylphenyl)propanol, 3-[3-(1-methylcyclohexyl)-4-methoxy-5-methylphenyl]propanol, 3-(3-t-butyl-4-methoxy-5-ethylphenyl)propanol, 3-(3-t-pentyl-4-methoxy-5-ethylphenyl)propanol, 3-(3-t-octyl-4-methoxy-5-ethylphenyl)propanol, 3-(3-cyclohexyl-4-methoxy-5-ethylphenyl)propanol, 3-[3-(1-methylcyclohexyl)-4-methoxy-5-ethylphenyl]propanol, 3-(3,5-di-t-butyl-2-methoxyphenyylpropanol, 3-(3,5-di-t-butyl-4-methoxyphenyl)propanol, 3-(3-t-pentyl-4-methoxy-5-t-butylphenyl)propanol, 3-(3-t-octyl-4-methoxy-5-t-butylphenyl)propanol, 3-(3-cyclohexyl-4-methoxy-5-t-buthylphenyl)propanol, 3-[3-(1-methylcyclohexyl)-4-methoxy-5-t-buthylphenyl]propanol, 3-(3-t-butyl-2-ethoxyphenyl)propanol, 3-(3-t-butyl-4-ethoxyphenyl)propanol, 3-(3-t-butyl-4-ethoxy-5-methylphenyl)propanol, 3-(3-t-butyl-2-ethoxy-5-methylphenyl)propanol, 3-(5-t-butyl-2-ethoxy-3-methylphenyl)propanol, 3-(3,5-di-t-butyl-4-methoxyphenyl)propanol, 3-(3,5-di-t-butyl-2-ethoxyphenyl)propanol, 4-(3-t-butyl-2-hydroxyphenyl)butanol, 4-(3-t-butyl-4-hydroxyphenyl)butanol, 4-(3-t-butyl-4-hydroxy-5-methylphenyl)butanol, 4-(3-t-butyl-2-hydroxy-5-methylphenyl)butanol, 4-(5-t-butyl-2-hydroxy-3-methylphenyl)butanol, 4-(3,5-di-t-butyl-4-hydroxyphenyl)butanol, 4-(3,5-di-t-butyl-2-hydroxyphenyl)butanol, 4-(3-t-butyl-2-methoxyphenyl)butanol, 4-(3-t-butyl-4-methoxyphenyl)butanol, 4-(3-t-butyl-4-methoxy-5-methylphenyl)butanol, 4-(3-t-butyl-2-methoxy-5-methylphenyl)butanol, 4-(5-t-butyl-2-methoxy-3-methylphenyl)butanol, 4-(3,5-di-t-butyl-4-methoxyphenyl)butanol, 4-(3,5-di-t-butyl-2-methoxyphenyl)butanol, 5-(3-t-butyl-2-hydroxyphenyl)pentanol, 5-(3-t-butyl-4-hydroxyphenyl)pentanol, 5-(3-t-butyl-4-hydroxy-5-methylphenyl)pentanol, 5-(3-t-butyl-2-hydroxy-5-methylphenyl)pentanol, 5-(5-t-butyl-2-hydroxy-3-methylphenyl)pentanol, 5-(3,5-di-t-butyl-4-hydroxyphenyl)pentanol, 6-(3,5-di-t-butyl-2-hydroxyphenyl)hexanol, 6-(3-t-butyl-2-hydroxyphenyl)hexanol, 6-(3-t-butyl-4-hydroxyphenyl)hexanol, 6-(3-t-butyl-4-hydroxy-5-methylphenyl)hexanol, 6-(3-t-butyl-2-hydroxy-5-methylphenyl)hexanol, 6-(5-t-butyl-2-hydroxy-3-methylphenyl)hexanol, 6-(3,5-di-t-butyl-4-hydroxyphenyl)hexanol and 6-(3,5-di-t-butyl-2-hydroxyphenyl)hexanol.

These compounds can be produced by reducing the corresponding phenylcarboxylic acids, or esters thereof, or benzaldehydes according to a known method.

Examples of the hydroxyl compound (XVII) wherein the connecting group F is represented by the formula (VIII) include 2-(3-t-butyl-2-hydroxyphenylmethyloxy)ethanol, 2-(3-t-butyl-4-hydroxyphenylmethyloxy)ethanol, 2-(3-t-butyl-2-hydroxy-5-methylphenylmethyloxy)ethanol, 2-(3,5-di-t-butyl-2-hydroxyphenylmethyloxy)ethanol, 2-3-t-butyl-4-hydroxy-5-methylphenylmethyloxy)ethanol, 2-(3,5-di-t-butyl-4-hydroxyphenylmethyloxy)ethanol, 2-(2-methyl-3,5-di-t-butyl-4-hydroxyphenylmethyloxy)ethanol, 2-(3-t-butyl-2-methoxyphenylmethyloxy)ethanol, 2-(3-t-butyl-4-methoxyphenylmethyloxy)ethanol, 2-(3-t-butyl-2-methoxy-5-methylphenylmethyloxy)ethanol, 2(3,5-di-t-butyl-2-methylphenylmethyloxy)ethanol 2-(3-t-butyl-4-methoxy-5-methylpherylmethyloxy)ethanol, 2-(3,5-di-t-butyl-4-methoxyphenylmethyloxy)ethanol, 2-(2-methyl-3,5-di-t-butyl-4-methoxyphenylmethyloxy)ethanol, 3-(3-t-butyl-2-hydroxylmeyphenylmethyloxy)panol, 3-(3-t-butyl-4-hydroxyphenylmethyloxy) propanol, 3-(3-t-butyl-2-hydroxy-5-methylphenylmethyloxy)propanol, 3-(3,5-di-t-butyl-2-hydroxyphenylmethyloxy)propanol, 3-(3-t-butyl-4-hydroxy-5-methylphenylmethyloxy)propanol, 3-(3,5-di-t-butyl-4-hydroxyphenylmethyloxy)propanol, 3-(2-methyl-3,5-di-t-butyl-4-hydroxyphenylmethyloxy)propanol, 3-(3-t-butyl-2-methoxyphenylmethloxy)propanol, 2-(3-t-butyl-4-methoxyphenylmethyloxy)propanol, 2-(3-t-butyl-2-methoxy-5-methylphenylmethyloxy)propanol, 2-(3,5-di-t-butyl-2-methoxyphenylmethyloxy)propanol, 2-(3-t-butyl-4-methoxy-5-methylphenylmethyloxy)propanol, 3-(3,5-di-t-butyl-4-methoxyphenylmethyloxy)propanol, 3-(2-methyl-3,5-di-t-butyl-4-methoxyphenylmethyloxy)propanol, 4-(3-t-butyl-2-hydroxyphenylmethyloxy)butanol, 4-(3-t-butyl-4-hydroxyphenylmethyloxy)butanol, 4-(3-t-butyl-2-hydroxy-5-methylphenylmethyloxy)butanol, 4-(3,5-di-t-butyl-2-hydroxyphenylmethyloxy)butanol, 4-(3-t-butyl-4-hydroxy-5-methylphenylmethyloxy)butanol, 4-(3,5-di-t-butyl-4-hydroxyphenylmethyloxy)butanol, 4-(2-methyl-3,5-di-t-butyl-4-hydroxylphenylmethyloxy)butanol, 4-(3-t-butyl-2-methoxyphenylmethyloxy)butanol 2-(3-t-butyl-4-methoxyphenylmethyloxy)butanol, 2-(3-t-butyl-2-methoxy-5-methyphenylmethyloxy )butanol, 2-(3,5-di-t-butyl-2-methoxyphenlmethyloxy)butanol, 2-(3-t-butyl-4-methoxy-5-methylphenylmethyloxy)butanol, 4-(3,5-di-t-butyl-4-methoxyphenylmethyloxy)butanol and 4-(2-methyl-3,5-di-t-butyl-4-methoxyphenylmethyloxy)butanol.

When the connecting group F is represented by the formula (VIII) and A is methylene, these compounds can be produced, for example, by reacting the corresponding diol with the corresponding phenol compound and formaldehyde. When A is an alkylene other than methylene, the compounds can be produced, for example, by reacting the corresponding diol with the corresponding halide.

Examples of the hydroxyl compound (XVII) wherein the connecting group F is represented by the formula (VII) include carboxylic acids such as 3-t-butyl-2-hydroxybenzoic acid, 3-t-butyl-4-hydroxybenzoic acid, 5-t-butyl-2-hydroxybenzoic acid, 3-t-pentyl-4-hydroxybenzoic acid, 3-t-octyl-4-hydroxybenzoic acid, 3-cyclohexyl-4-hydroxybenzoic acid, 3-(1-methylcyclohexyl)-4-hydroxybenzoic acid, 3-t-butyl-2-hydroxy-5-methylbenzoic acid, 3-t-butyl-4-hydroxy-5-methylbenzoic acid, 5-t-butyl-2-hydroxy-3-methylbenzoic acid, 3-t-pentyl-4-hydroxy-5-methylbenzoic acid, 3-t-octyl-4-hydroxy-5-methylbenzoic acid, 3-cyclohexyl-4-hydroxy-5-methylbenzoic acid, 3-(1-methylcyclohexyl)-4-hydroxy-5-methylbenzoic acid, 3-t-butyl-4-hydroxy-5-ethylbenzoic acid, 3-t-pentyl-4-hydroxy-5-ethylbenzoic acid, 3-t-octyl-4-hydroxy-5-ethylbenzoic acid, 3-cyclohexyl-4-hydroxy-5- ethylbenzoic acid, 3-(1-methylcyclohexyl)-4-hydroxy-5-ethylbenzoic acid, 3,5-di-t-butyl-2-hydroxybenzoic acid, 3,5-di-t-butyl-4-hydroxybenzoic acid, 3-t-pentyl-4-hydroxy-5-t-butylbenzoic acid, 3-t-octyl-4-hydroxy-5-t-butylbenzoic acid, 3-cyclohexyl-4-hydroxy-5-t-butylbenzoic acid, 3-(1-methylcyclohexyl)-4-hydroxy-5-t-butylbenzoic acid, 3-t-butyl-2-methoxybenzoic acid, 3-t-butyl-4-methoxybenzoic acid, 3-t-butyl-5-methoxybenzoic acid, 3-t-pentyl-4-methoxybenzoic acid, 3-t-octyl-4-methoxybenzoic acid, 3-cyclohexyl-4-methoxybenzoic acid, 3-(1-methylcyclohexyl)-4-methoxybenzoic acid, 3-t-butyl-2-methoxy-5-methylbenzoic acid, 3-t-butyl-4-methoxy-5-methylbenzoic acid, 5-t-butyl-2-methoxy-3-methylbenzoic acid, 3-t-pentyl-4-methoxy-5-methylbenzoic acid, 3-t-octyl-4-methoxy-5-methylbenzoic acid, 3-cyclohexyl-4-methoxy-5-methylbenzoic acid, 3-(1-methylcyclohexyl)-4-methoxy-5-methylbenzoic acid, 3-t-butyl-4-methoxy-5-ethylbenzoic acid, 3-t-pentyl-4-methoxy-5-ethylbenzoic acid, 3-t-octyl-4-methoxy-5-ethylbenzoic acid, 3-cyclohexyl-4-methoxy-5-ethylbenzoic acid, 3-(11-methylcyclohexyl)-4-methoxy-5-ethylbenzoic acid, 3,5-di-t-butyl-2-methoxybenzoic acid, 3,5-di-t-butyl-4-methoxybenzoic acid, 3-t-pentyl-4-methoxy-5-t-butylbenzoic acid, 3-t-octyl-4-methoxy-5-t-butylbenzoic acid, 3-cyclohexyl-4-methoxy-5-t-butylbenzoic acid, 3-(3-(1-methylcyclohexyl)-4-methoxy-5-t-butylbenzoic acid, 3-t-butyl-2-ethoxybenzoic acid, 3-t-butyl-4-ethoxybenzoic acid, 3-t-butyl-4-ethoxy-5-methylbenzoic acid, 3-t-butyl-2-ethoxy-5-methylbenzoic acid, 5-t-butyl-2-ethoxy-3-methylbenzoic acid, 3,5-di-t-butyl-4-ethoxybenzoic acid, 3,5-di-t-butyl-2-ethoxybenzoic acid, (3-t-butyl-2-hydroxyphenyl)acetic acid, (3-t-butyl-4-hydroxyphenyl)acetic acid, (5-t-butyl-2-hydroxyphenyl)acetic acid, (3-t-pentyl-4-hydroxyphenyl)acetic acid, (3-t-octyl-4-hydroxyphenyl)acetic acid, (3-cyclohexyl-4-hydroxyphenyl)acetic acid, [3-(1-methylcyclohexyl)-4-hydroxyphenyl]acetic acid, (3-t-butyl-2-hydroxy-5-methylphenyl)acetic acid, (3-t-butyl-4-hydroxy-5-methylphenyl)acetic acid, (5-t-butyl-2-hydroxy-3-methylphenyl)acetic acid, (3-t-pentyl-4-hydroxy-5-methylphenyl)acetic acid, (3-t-octyl-4-hydroxy-5-methylphenyl)acetic acid, (3-cyclohexyl-4-hydroxy-5-methylphenyl)acetic acid, [3-(1-methylcyclohexyl)-4-hydroxy-5-methylphenyl]acetic acid, (3-t-butyl-4-hydroxy-5-ethylphenyl)acetic acid, (3-t-pentyl-4-hydroxy-5-ethylphenyl)acetic acid, (3-t-octyl-4-hydroxy-5-ethylphenyl)acetic acid, (3-cyclohexy-4-hydroxy-5-ethylohenyl)acetic acid, [3-(1-methylcyclohexyl)-4-hydroxy-5-ethylphenyl]acetic acid, (3,5-di-t-butyl-2-hydroxyphenyl)acetic acid, (3,5-di-t-butyl-4-hydroxyphenyl)acetic acid, (3-t-oentyl-4-hydroxy-5-t-butyphenyl)acetic acid, (3-t-octyl-4-hydroxy-5-t-butylphenyl)acetic acid, (3-cyclohexyl-4-hydroxy-5-t-butylphenyleacetic acid, [3-(1-methylcyclohexyl)-4-hydroxy-5-t-butylphenyl]acetic acid, (3-t-butyl-2-methoxyphenyl)acetic acid, (3-t-butyl-4-methoxyphenyl)acetic acid, (3-t-butyl-5-methoxyphenyl)acetic acid, (3-t-pentyl-4-methoxyphenyl)acetic acid, (3-t-octyl-4-methoxyphenyl)acetic acids (3-cyclohexyl-4-methoxyphenyl)acetic acid, [3-(1-methylcyclohexyl)-4-methoxyphenyl]acetic acid, (3-t-butyl-2-methoxy-5-methylphenyl)acetic acid, (3-t-butyl-4-methoxy-5-methylphenyl)acetic acid, (5-t-butyl-2-methoxy-3-methylphenyl)acetic acid, (3-t-pentyl-4-methoxy-5-methylphenyl)acetic acid, (3-t-octyl-4-methoxy-5-methylphenyl)acetic acid, (3 -cyclohexyl-4-methoxy-5-methylphenyl)acetic acid, 3-(1-methylcyclohexyl)-4-methoxy-5-methylphenyl acetic acid, (3-t-butyl-4-methoxy-5-ethylphenyl)acetic acid, (3-t-pentyl-4-methoxy-5-ethylphenyl)acetic acid, (3-t-octyl-4-methoxy-5-ethylphenyl)acetic acid, (3-cyclohexyl-4-methoxy-5-ethylphenyl)acetic acid, [3-(1-methylcyclohexyl)-4-methoxy-5-ethylphenyl]acetic acid, (3,5-di-t-butyl-2-methoxyphenyl)acetic acid, (3,5-di-t-butyl-4-methoxyphenyl)acetic acid, (3-t-pentyl-4-methoxy-5-t-butylhenyl)acetic acid, (3-t-octyl-4-methoxy-5-t-butylphenyl)acetic acid, (3-cyclohexyl-4-methoxy-5-t-butylphenyl)acetic acid, [3-(1-nmethylcyclohexyl)-4-methoxy-5-t-butylphenyl]acetic acid, (3-t-butyl-2-ethoxyphenyl)acetic acid, (3-t-butyl-4-ethoxyphenyl)acetic acid, (3-t-butyl-4-ethoxy-5-ethylphenyl)acetic acid, (3-t-butyl-2-ethoxy-5-methylphenyl)acetic acid, (5-t-butyl-2-ethoxy-3-methylphenyl)acetic acid, (3,5-di-t-butyl-4-ethoxyphenyl)acetic acid, (3,5-di-t-butyl-2-ethoxyphenyl) acetic acid, 3-(3-t-butyl-2-hydroxyphenyl)propionic acid, 3-(3-t-butyl-4-hydroxyphenyl)propionic acid, 3-(5-t-butyl-2-hydroxyphenyl)propionic acid, 3-(3-t-penty-4-hydroxyphenyl)propionic acid, 3-(3-t-octyl-4-hydroxyphenyl)propionic acid, 3-(3-cyclohexyl-4-hydroxyphenyl)propionic acid, 3-[3-(1-methylcyclohexyl)-4-hydroxyphenyl]propionic acid, 3-(3-t-butyl-2-hydroxy-5-methylohenyl)propionic acid, 3 -(3-t-butyl-4-hydroxy-5-methylphenyl)propionic acid, 3-(5-t-butyl-2-hydroxy-3-methylphenyl)propionic acid, 3-(3-t-pentyl-4-hydroxy-5-methylphenyl)propionic acid, 3-(3-t-octyl-4-hydroxy-5-methylphenyl)propionic acid, 3-(3-cyclohexyl-4-hydroxy-5-methylphenyl)propionic acid, 3-[3-(1-methylcyclohexyl)-4-hydroxy-5-methylphenyl]propionic acid, 3-(3-t-butyl-4-hydroxy-5-ethylphenyl)propionic acid, 3-(3-t-pentyl-4-hydroxy-5-ethylphenyl)propionic acid, 3-(3-t-octyl-4-hydroxy-5-ethylphenyl)propionic acid, 3-(3-cyclohexyl-4-hydroxy-5-ethylphenyl)propionic acid, 3-[3-(1-methylcyclohexyl)-4-hydroxy-5-ethylphenyl]propionic acid, 3-(3,5-di-t-butyl-2-hydroxyphenyl)propionic acid, 3-(3,5-di-t-butyl-4-hydroxyphenyl)propionic acid, 3-(3-t-pentyl-4-hydroxy-5-t-butylphenyl)propionic acid, 3-(3-t-octyl-4-hydroxy-5-t-butylphenyl)propionic acid, 3-(3-cyclohexyl-4-hydroxy-5-t-butylphenyl)propionic acid, 3-[3-(1-methylcyclohexyl)-4-hydroxy-5-t-butylphenyl]propionic acid, 3-(3-t-butyl-2-methoxyphenyl)propionic acid, 3-(3-t-butyl-4-methoxyphenyl)propionic acid, 3-(3-t-butyl-5-methoxyphenyl)propionic acid, 3-(3-t-pentyl-4-methoxyphenyl)pronionic acid, 3-(3-t-octyl-4-methoxyphenyl)propionic acid, 3-(3-cyclohexyl-4-methoxyphenyl)propionic acid, 3-[3-(1-methylcyclohexyl)-4-methoxyphenylipropionic acid, 3-(3-t-butyl-2-methoxy-5-methylphenyl)propionic acid, 3-(3-t-butyl-4-methoxy-5-methylphenyl)propionic acid, 3-(5-t-butyl-2-methoxy-3-methylphenyl)propionic acid, 3-(3-t-pentyl-4-methoxy-5-methylphenyl)propionic acid, 3-(3-t-octyl-4-methoxy-5-methylphenyl)propionic acid, 3-(3-cyclohexyl-4-methoxy-5-methylphenyl)propionic acid, 3-[3-(1-methylcyclohexyl)-4-methoxy-5-methylphenyl]propionic acid, 3-(3-t-butyl-4-methoxy-5-ethylphenyl)propionic acid, 3-(3-t-pentyl-4-methoxy-5-ethylphenyl)propionic acid, 3-(3-t-octyl-4-methoxy-5-ethylphenyl)propionic acid, 3-(-3-cyclohexyl-4-methoxy-5-ethylphenyl)propionic acid, 3-[3-(1-methylcyclohexyl)-4-methoxy-5-ethylphenyl]propionic acid, 3-(3,5-di-t-butyl-2-methoxyphenyl)propionic acid, 3-(3,5-di-t-butyl-4-methoxyphenyl)propionic acid, 3-(3-t-pentyl-4-methoxy-5-t-butylphenyl)propionic acid, 3-(3-t-octyl-4-methoxy-5-t-butylphenyl)propionic acid, 3-(3-cyclohexyl-4-methoxy-5-t-butylphenyl)propionic acid, 3-[3-(1-methylcyclohexyl)-4-methoxy-5-t-butylphenyl]

propionic acid, 3-(3-t-butyl-2-ethoxyphenyl)propionic acid, 3-(3-t-butyl-4-ethoxyphenyl)propionic acids 3-(3-t-butyl-4-ethoxy-5-methylphenyl)propionic acid, 3-(3-t-butyl-2-ethoxy-5-methylphenyl)propionic acid, 3-(5-t-butyl-2-ethoxy-3-methylphenyl)propionic acid, 3-(3,5-di-t-butyl-4-ethoxyphenyl)propionic acid, 3-(3,5-di-t-butyl-2-ethoxyphenyl)propionic acid, 3-(3-t-butyl-2-hydroxyphenyl)butanoic acid, 3-(3 -t-butyl-4-hydroxyphenyl)butanoic acid, 3-(3-t-butyl-4-hydroxy-5-methylphenyl)butanoic acid, 3-(3-t-butyl-2-hydroxy-5-methylphenyl)butanoic acid, 3-(5-t-butyl-2-hydroxy-3-methylphenyl)butanoic acid, 3-(3,5-di-t-butyl-4-hydroxyphenyl)butanoic acid, 3-(3,5-di-t-butyl-2-hydroxyphenyl)butanoic acid, 3-(3-t-butyl-2-methoxyphenyl)butanoic acid, 3-(3-t-butyl-4-methoxyphenyl)butanoic acid, 3-(3-t-butyl-4-methoxy-5-methylphenyl)butanoic acid, 3-(3-t-butyl-2-methoxy-5-methylphenyl)butanoic acid, 3-(5-t-butyl-2-methoxy-3-methylphenyl)butanoic acid, 3-(3,5-di-t-butyl-4-methoxyphenyl)butanoic acid and 3-(3,5-di-t-butyl-2-methoxyphenyl)butanoic acid.

Such carboxylic acids of formula XVII wherein the connecting group F is represented by the formula (VII) and A is a direct bond can be produced, for example, by subjecting the corresponding hydroxybenzoic acid, alkoxybenzoic acid, aralkyloxybenzoic acid, etc. to the Friedal-Crafts reaction using a catalyst such as aluminum chloride or zinc chloride.

The carboxylic acids of fomula XVII wherein $R^B$ is represented by formula (XIV) and Z is a hydroxyl group, an alkoxy group or an aralkyloxy group, can also be produced, for example, by carrying out the Kolbe-Schmitt reaction using the corresponding phenols, alkali metals hydroxides such as sodium chloride, potassium chloride, and carbon dioxide according to the methods described in JP-A-62-61949 and JP-A-63-165341.

In addition, when the connecting group F is represented by the formula (VIII) and A is an alkylene having 1 to 8 carbon atoms, the compounds can be produced by acylating the corresponding phenol using a Friedel-Crafts catalyst, such as aluminum chloride and zinc chloride, and carboalkoxyalkanoylhalogenoide, reducing a carbonyl group at the benzyl position with a hydrogenation catalyst such as carbon palladium or carbon platinum to convert into an alkylene followed by hydrolyzing the ester with an acid or alkali, according to the method described in Rubber Chemistry and Technology 46, 96(1973).

Examples of the hydroxyl compound (XVII) wherein the connecting group F is a group of formula (IX) include 2-hydroxyethyl benzoate, 2-hydroxyethyl 3-t-butyl-2-hydroxybenzoate, 2-hydroxyethyl 3-t-butyl-4-hydroxybenzoate, 2-hydroxyethyl 3-t-butyl-5-hydroxybenzoate, 2-hydroxyethyl 3-t-pentyl-4-hydroxybenzoate, 2-hydroxyethyl 3-t-octyl-4-hydroxybenzoate, 2-hydroxyethyl 3-cyclohexyl-4-hydroxybenzoate, 2-hydroxyethyl 3-(1-methylcyclohexyl)-4-hydroxybenzoate, 2-hydroxyethyl 3-t-butyl-2-hydroxy-5-methylbenzoate, 2-hydroxyethyl 3-t-butyl-4-hydroxy-5-methylbenzoate, 3-hydroxypropyl 3-t-butyl-4-hydroxy-5-methylbenzoate, 4-hydroxybutyl 3-t-butyl-4-hydroxy-5-methylbenzoate, 2-hydroxyethyl 5-t-butyl-2-hydroxy-3-methylbenzoate, 2-hydroxyethyl 3-t-pentyl-4-hydroxy-5-methylbenzoate, 2-hydroxyethyl 3-t-octyl-4-hydroxy-5-methylbenzoate, 2-hydroxyethyl 3-cyclohexyl-4-hydroxy-5-methylbenzoate, 2-hydroxyethyl 3-(1-methylcyclohexyl)-4-hydroxy-5-methylbenzoate, 2-hydroxyethyl 3-t-butyl-4-hydroxy-5-ethylbenzoate, 2-hydroxyethyl 3-t-pentyl-4-hydroxy-5-ethylbenzoate, 2-hydroxyethyl 3-t-octyl-4-hydroxy-5-ethylbenzoate, 2-hydroxyethyl 3-cyclohexyl-4-hydroxy-5-ethylbenzoate, 2-hydroxyethyl 3-(1-methylcyclohexyl)-4-hydroxy-5-ethylbenzoate, 2-hydroxyethyl 3,5-di-t-butyl-2-hydroxybenzoate, 2-hydroxyethyl 3,5-di-t-butyl-4-hydroxybenzoate, 3-hydroxypropyl 3,5-di-t-butyl-4-hydroxybenzoate, 4-hydroxybutyl 3,5-di-t-butyl-4-hydroxybenzoate, 2-hydroxyethyl 3-t-pentyl-4-hydroxy-5-t-butylbenzoate, 2-hydroxyethyl 3-t-octyl-4-hydroxy-5-t-butylbenzoate, 2-hydroxyethyl 3-cyclohexyl-4-hydroxy-5-t-butylbenzoate, 2-hydroxyethyl 3-(3-(1-methylcyclohexyl)-4-hydroxy-5-t-butylbenzoate, 2-hydroxyethyl (3-t-butyl-4-hydroxyphenyl) acetate, 2-hydroxyethyl (3-t-butyl-5-hydroxyphenyl)acetate, 2-hydroxyethyl (3-t-pentyl-4-hydroxyphenyl)acetate, 2-hydroxyethyl (3-t-octyl-4-hydroxyphenyl)acetate, 2-hydroxyethyl (3-cyclohexyl-4-hydroxyphenyl)acetate, 2-hydroxyethyl [3-(1-methylcyclohexyl)-4-hydroxyphenyl] acetate, 2-hydroxyethyl (3-t-butyl-2-hydroxy-5-methylphenyl)acetate, 2-hydroxyethyl (3-t-butyl-4-hydroxy-5-methylphenyl)acetate, 3-hydroxypropyl (3-t-butyl-4-hydroxy-5-methylphenyl)acetate, 4-hydroxybutyl (3-t-butyl-4-hydroxy-5-methylphenyl)acetate, 2-hydroxyethyl (5-t-butyl-2-hydroxy-3-methylphenyl) acetate, 2-hydroxyethyl (3-t-pentyl-4-hydroxy-5-methylphenyl)acetate, 2-hydroxyethyl (3-t-octyl-4-hydroxy-5-methylphenyl)acetate, 2-hydroxyethyl (3-cyclohexyl-4-hydroxy-5-methylphenyl)acetate, 2-hydroxyethyl [3-(1-methylcyclohexyl)-4-hydroxy-5-methylphenyl)acetate, 2-hydroxyethyl (3-t-butyl-4-hydroxy-5-ethylphenyl)acetate, 2-hydroxyethyl (3-t-pentyl-4-hydroxy-5-ethylphenyl)acetate, 2-hydroxyethyl (3-t-octyl-4-hydroxy-5-ethylphenyl)acetate, 2-hydroxyethyl (3-cyclohexyl-4-hydroxy-5-ethylphenyl)acetate, 2-hydroxyethyl [3-(1-methylcyclohexyl)-4-hydroxy-5-ethylphenyl)acetate, 2-hydroxyethyl (3,5-di-t-butyl-2-hydroxyphenyl)acetate, 2-hydroxyethyl (3,5-di-t-butyl-4-hydroxyphenyl)acetate, 3-hydroxypropyl (3,5-di-t-butyl-4-hydroxyphenyl)acetate, 4-hydroxybutyl (3,5-di-t-butyl-4-hydroxyphenyl)acetate, 2-hydroxyethyl (3-t-pentyl-4-hydroxy-5-t-butylphenyl)acetate, 2-hydroxyethyl (3-t-octyl-4-hydroxy-5-t-butylphenyl)acetate, 2-hydroxyethyl (3-cyclohexyl-4-methoxy-5-t-butylphenyl)acetate, 2-hydroxyethyl [3-(1 -methylcyclohexyl)-4-hydroxy-5-t-butylphenyl]acetate, 2-hydroxyethyl 3-(3-t-butyl-2-hydroxyphenyl)propionate, 2-hydroxyethyl 3-(3-t-butyl-4-hydroxyphenyl)propionate, 2-hydroxyethyl 3-(3-t-butyl-5-hydroxyphenyl)propionate, 2-hydroxyethyl 2-,(3-t-pentyl-4-hydroxyphenyl)propionate, 2-hydroxyethyl 3-(3-t-octyl-4-hydroxyphenyl)propionate, 2-hydroxyethyl 3-(3-t-cyclohexyl-4-hydroxyphenyl)propionate, 2-hydroxyethyl 3-[3-(1-methylcyclohexyl)-4-hydroxyphenyl]propionate, 2-hydroxyethyl 3-(3-t-butyl-2-hydroxy-5-methylphenyl) propionate, 2-hydroxyethyl 3-(3-t-butyl-4-hydroxy-5-methylphenyl)propionate, 3-hydroxybutyl 3-(3-t-butyl-4-hydroxy-5-methylphenyl)propionate, 4-hydroxybutyl 3-(3-t-butyl-4-hydroxy-5-methylphenyl)propionate, 2-hydroxyethyl 3-(5-t-butyl-2-hydroxy-3-methylphenyl) propionate, 2-hydroxyethyl (3-t-pentyl-4-hydroxy-5-methylphenyl)propionate, 2-hydroxyethyl 3-(3-t-octyl-4-hydroxy-5-methylphenyl)propionate, 2-hydroxyethyl 3-(3-cyclohexyl-4-hydroxy-5-methylphenyl)propionate, 2-hydroxyethyl 3-[3-(1-methylcyclohexy)-4-hydroxy-5-methylphenyl]propionate, 2-hydroxyethyl 3-(3-t-butyl-4-hydroxy-5-ethylphenyl)propionate, 2-hydroxyethyl 3-(3-t-pentyl-4-hydroxy-5-ethylphenyl)propionate, 2-hydroxyethyl 3-(3-t-octyl-4-hydroxy-5-ethylphenyl)

propionate, 2-hydroxyethyl 3-(3-cyclohexyl-4-hydroxy-5-ethylphenyl)propionate, 2-hydroxyethyl 3-[3-1-methylcyclohexyl)-4-hydroxy-5-ethylphenyl]propionate, 2-hydroxyethyl 3-(3,5-di-t-butyl-2-hydroxyphenyl) propionate, 2-hydroxyethyl 3-(3,5-di-t-butyl-4-hydroxyphenyl)propionate, 3-hydroxypropyl 3-(3,5-di-t-butyl-4-hydroxyphenyl)propionate, 4-hydroxybutyl 3-(3,5-di-t-butyl-4-hydroxyphenyl)propionate, 2-hydroxyethyl 3-(3-t-pentyl-4-hydroxy-5-t-butylphenyl)propionate, 2-hydroxyethyl 3-(3-t-octyl-4-hydroxy-5-t-butylphenyl) propionate, 2-hydroxyethyl 3-(3-cyclohexyl-4-hydroxy-5-t-butylphenyl)propionate, 2-hydroxyethyl 3-[3-(1-methylcyclohexyl)-4-hydroxy-5-t-butylphenyl]propionate, 2-hydroxyethyl 4-(3-t-butyl-2-hydroxyphenyl)butyrate, 2-hydroxyethyl 4-(3-t-butyl-4-hydroxyphenyl)butyrate, 2-hydroxyethyl 4-(3-t-butyl-4-hydroxy-5-methylphenyl) butyrate, 3-hydroxypropyl 4-(3-t-butyl-4-hydroxy-5-methylphenyl)butyrate, 4-hydroxybutyl 4-(3-t-butyl-4-hydroxy-5-methylphenyl)butyrate, 2-hydroxyethyl 4-(3-t-butyl-2-hydroxy-5-methylphenyl)butyrate, 2-hydroxyethyl 4-(5-t-butyl-2-hydroxy-3-methylphenyl)butyrate, 2-hydroxyethyl 4-(3,5-di-t-butyl-4-hydroxyphenyl)butyrate, 3-hydroxypropyl 4-(3,5-di-t-butyl-4-hydroxyphenyl) butyrate, 4-hydroxybutyl 4-(3,5-di-t-butyl-4-hydroxyphenyl)butyrate, 2-hydroxyethyl 4-(3,5-di-t-butyl-4-hydroxyphenyl)butyrate, 2-hydroxyethyl 3-t-butyl-2methoxybenzoate, 2-hydroxyethyl 3-t-butyl-4-methoxybenzoate, 2-hydroxyethyl 3-t-butyl-5-methoxybenzoate, 2-hydroxyethyl 3-t-pentyl-4-methoxybenzoate, 2-hydroxyethyl 3-t-octyl-4-methoxybenzoate, 2-hydroxyethyl 3-cyclohexyl-4-methoxybenzoate, 2-hydroxyethyl 3-(1-methylcyclohexyl)-4-methoxybenzoate, 2-hydroxyethyl 3-t-butyl-2-methoxy-5-methylbenzoate, 2-hydroxyethyl 3-t-butyl-4-methoxy-5-methylbenzoate, 3-hydroxypropyl 3-t-butyl-4-methoxy-5-methylbenzoate, 4-hydroxybutyl 3-t-butyl-4-methoxy-5-methylbenzoate, 2-hydroxyethyl 5-t-butyl-2-methoxy-3-methylbenzoate, 2-hydroxyethyl 3-t-pentyl-4-methoxy-5-methylbenzoate, 2-hydroxyethyl 3-t-octyl-4-methoxy-5-methylbenzoate, 2-hydroxyethyl 3-cyclohexyl-4-methoxy-5-methylbenzoate, 2-hydroxyethyl 3-(1-methylcyclohexyl)-4-methoxy-5-methylbenzoate, 2-hydroxyethyl 3-t-butyl-4-methoxy-5-ethylbenzoate, 2-hydroxyethyl 3-t-pentyl-4-methoxy-5-ethylbenzoate, 2-hydroxyethyl 3-t-octyl-4-methoxy-5-ethylbenzoate, 2-hydroxyethyl 3-cyclohexyl-4-methoxy-5-ethylbenzoate, 2-hydroxyethyl 3-(1-methylcyclohexyl)-4-methoxy-5-ethylbenzoate, 2-hydroxyethyl 3,5-di-t-butyl-2-methoxybenzoate, 2-hydroxyethyl 3,5-di-t-butyl-4-methoxybenzoate, 3-hydroxypropyl 3,5-di-t-butyl-4-methoxybenzoate, 4-hydroxybutyl 3,5-di-t-butyl-4-methoxybenzoate, 2-hydroxyethyl 3-t-mentyl-4-methoxy-5-t-butylbenzoate, 2-hydroxyethyl 3-t-octyl-4-methoxy-5-t-butylbenzoate, 2-hydroxyethyl 3-cyclohexyl-4-methoxy-5-t-butylbenzoate, 2-hydroxyethyl 3-(3-(1-methylcyclohexyl)-4-methoxy-5-t-butylbenzoate, 2-hydroxyethyl 3-t-butyl-2-ethoxybenzoate, 2-hydroxyethyl 3-t-butyl-4-ethoxybenzoate, 2-hydroxyethyl 3-t-butyl-4-ethoxy-5-methylbenzoate, 3-hydroxypropyl 3-t-butyl-4-ethoxy-5-methylbenzoate, 4-hydroxybutyl 3-t-butyl-4-ethoxy-5-methylbenzoate, 2-hydroxyethyl 3-t-butyl-2-ethoxy-5-methylbenzoate, 2-hydroxyethyl 5-t-butyl-2-ethoxy-3-methylbenzoate, 2-hydroxyethyl 3,5-di-t-butyl-4-ethoxybenzoate, 2-hydroxyethyl 3,5-di-t-butyl-2-ethoxybenzoate, 2-hydroxyethyl (3-t-butyl-4-methoxyphenyl)acetate, 2-hydroxyethyl (3-t-butyl-5-methoxyphenyl)acetate, 2-hydroxyethyl (3-t-pentyl-4-methoxypnhenyl)acetate, 2-hydroxyethyl (3-t-octyl-4-methoxyphenyl)acetate, 2-hydroxyethyl (3-cyclohexyl-4-methoxyphenyl)acetate, 2-hydroxyethyl [3-(1-methylcyclohexyl)-4-methoxypheny]acetate, 2-hydroxyethyl (3-t-butyl-2-methoxy-5-methylphenyl) acetate, 2-hydroxyethyl 3-(3-t-butyl-4-methoxy-5-methylphenyl)acetate, 3-hydroxypropyl (3-t-butyl-4-methoxy-5-methylphenyl)acetate, 4-hydroxybutyl (3-t-butyl-4-methoxy-5-methylphenyl)acetate, 2-hydroxyethyl (5-t-butyl-2-methoxy-3-methylphenyl)acetate, 2-hydroxyethyl (3-t-pentyl-4-methoxy-5-methylphenyl) acetate, 2-hydroxyethyl (3-t-octyl-4-methoxy-5-methylphenyl)acetate, 2-hydroxyethyl (3-cyclohexyl-4-methoxy-5-methylphenyl)acetate, 2-hydroxyethyl [3-(1-methylcyclohexyl)-4-methoxy-5-methylphenyl]acetate, 2-hydroxyethyl (3-t-butyl-4 -methoxy-5-ethylphenyl) acetate, 2-hydroxyethyl (3-t-pentyl-4-methoxy-5-ethylphenyl)acetate, 2-hydroxyethyl (3-t-octyl-4-methoxy-5-ethylphenyl)acetate, 2-hydroxyethyl (3-cyclohexyl-4-methoxy-5-ethylphenyl)acetate, 2-hydroxyethyl [3-(1-methylcyclohexyl)-4-methoxy-5-ethylphenyl]acetate, 2-hydroxyethyl (3,5-di-t-butyl-2-methoxyphenyl)acetate, 2-hydroxyethyl (3,5-di-t-butyl-4-methoxyphenyl)acetate, 3-hydroxypropyl (3,5-di-t-butyl-4-methoxyphenyl)acetate, 4-hydroxybutyl (3,5-di-t-butyl-4-methoxyphenyl)acetate, 2-hydroxyethyl (3-t-pentyl-4-methoxy-5-t-butylphenyl) acetate, 2-hydroxyethyl (3-t-octyl-4-hydroxy-5-t-butylphenyl)acetate, 2-hydroxyethyl (3-cyclohexyl-4-hydroxy-5-t-butylphenyl)acetate, 2-hydroxyethyl [3-(1-methylcyclohexyl)-4-methoxy-5-t-butylphenyl]acetate, 2-hydroxyethyl (3-t-butyl-2-ethoxyphenyl)acetate; 2-hydroxyethyl (3-t-butyl-4-ethoxyphenyl)acetate, 2-hydroxyethyl (3-t-butyl-4-ethoxy-5-methylphenyl) acetate, 3-hydroxypropyl (3-t-butyl-4-ethoxy-5-methylphenyl)acetate, 4-hydroxybutyl (3-t-butyl-4-ethoxy-5-methylphenyl)acetate, 2-hydroxyethyl (3-t-butyl-2-ethoxy-5-methylphenyl)acetate, 2-hydroxyethyl (3-t-butyl-2-ethoxy-5-methylphenyl)acetate, 2-hydroxyethyl (5-t-butyl-2-ethoxy-3-methylphenyl)acetate, 2-hydroxyethyl (3,5-di-t-butyl-4-ethoxyphenyl)acetate, 3-hydroxypropyl (3,5-di-t-butyl-4-ethoxyphenyl)acetate, 4-hydroxybutyl (3,5-di-t-butyl-4-ethoxyphenyl)acetate, 2-hydroxyethyl (3,5-di-t-butyl-2-ethoxyphenyl)acetate, 2-hydroxyethyl 3-(3-t-butyl-2-methoxyphenyl)propionate, 2-hydroxyethyl 3-(3-t-butyl-4-methoxyphenyl)propionate, 2-hydroxyethyl 3-(3-t-butyl-5-methoxyphenyl)propionate, 2-hydroxyethyl 2-,(3-t-pentyl-4-methoxyphenyl)propionate, 2-hydroxyethyl 3-(3-t-octyl-4-methoxyphenyl)propionate, 2-hydroxyethyl 3-(3-cyclohexyl-4-methoxyphenyl)propionate, 2-hydroxyethyl 3-[3-(1-methylcyclohexyl)-4-methoxyphenyl]propionate, 2-hydroxyethyl 3-(3-t-butyl-2-methoxy-5-methylphenyl)propionate, 2-hydroxyethyl 3-(3-t-butyl-4-methoxy-5-methylphenyl)propionate, 3-hydroxybutyl 3-(3-t-butyl-4-methoxy-5-methylphenyl) propionate, 4-hydroxybutyl 3-(3-t-butyl-4-methoxy-5-methylphenyl)propionate, 2-hydroxyethyl 3-(5-t-butyl-4-methoxy-3-methylphenyl)propionate, 2-hydroxyethyl 3-(3-t-pentyl-4-methoxy-5-methylphenyl)propionate, 2-hydroxyethyl 3-(3-t-octyl-4-methoxy-5-methylphenyl) propionate, 2-hydroxyethyl 3-(3-cyclohexyl-4-methoxy-5-methylphenyl)propionate, 2-hydroxyethyl 3-[3-(1-methylcyclohexyl)-4-methoxy-5-methylphenyl]propionate, 2-hydroxyethyl 3-(3-t-butyl-4-methoxy-5-ethylphenyl) propionate, 2-hydroxyethyl 3-(3-t-pentyl-4-methoxy-5-ethylphenyl)propionate, 2-hydroxyethyl 3-(3-t-octyl-4-methoxy-5-ethylphenyl)propionate, 2-hydroxyethyl 3-(3-cyclohexyl-4-methoxy-5-ethylphenyl)propionate, 2-hydroxyethyl 3-[3-(1-methylcyclohexyl)-4-methoxy-5- ethylphenyl]propionate, 2-hydroxyethyl 3-(3,5-di-t-butyl-2-methoxyphenyl)propionate 2-hydroxyethyl 3-(3,5-di-t-butyl-4-methoxyphenyl)propionate, 3-hydroxypropyl 3-(3,5-di-t-butyl-4-methoxyphenyl)propionate, 4-hydroxybutyl 3-(3,5-di-t-butyl-4-methoxyphenyl)propionate, 2-hydroxyethyl 3-(3-t-pentyl-4-methoxy-5-t-butylphenyl)propionate, 2-hydroxyethyl 3-(3-t-octyl-4-methoxy-5-t-butylphenyl)propionate, 2-hydroxyethyl 3-(3-cyclohexyl-4-methoxy-5-t-butylphenyl)propionate, 2-hydroxyethyl 3-[3-(1-methylcyclohexyl)-4-methoxy-5-t-butylphenyl]propionate, 2-hydroxyethyl 3-(3-t-butyl-2-ethoxyphenyl)propionate, 2-hydroxyethyl 3-(3-t-butyl-4-ethoxyphenyl)propionate, 2-hydroxyethyl 3-(3-t-butyl-4-ethoxy-5-methylphenyl)propionate, 3-hydroxypropyl 3-(3-t-butyl-4-ethoxy-5-methylphenyl)propionate, 4-hydroxybutyl 3-(3-t-butyl-2-ethoxy-5-methylphenyl)propionate, 2-hydroxyethyl 3-(5-t-butyl-2-ethoxy-3-methylphenyl)propionate, 2-hydroxyethyl 3-(3,5-di-t-butyl-4-ethoxyphenyl)propionate, 3-hydroxypropyl 3-(3,5-di-t-butyl-4-ethoxyphenyl)propionate, 4-hydroxybutyl 3-(3,5-di-t-butyl-4-ethoxyphenyl)propionate, 2-hydroxyethyl 3-(3,5-di-t-butyl-2-ethoxyphenyl)propionate, 2-hydroxyethyl 4-(3-t-butyl-2-methoxylphenyl)butyrate, 2-hydroxyethyl 4-(3-t-butyl-4-methoxyphenyl)butyrate, 2-hydroxyethyl 4-(3-t-butyl-4-methoxy-5-methylphenyl)butyrate, 3-hydroxypropyl 4-(3-t-butyl-4-methoxy-5-methylphenyl)butyrate, 4-hydroxybutyl 4-(3-t-butyl-4-methoxy-5-methylphenyl)butyrate, 2-hydroxyethyl 4-(3-t-butyl-2-methoxy-5-methylphenyl)butyrate, 2-hydroxyethyl 4-(5-t-butyl-2-methoxy-3-methylphenyl)butyrate, 2-hydroxyethyl 4-(3,5-di-t-butyl-4-methoxyphenyl)butyrate, 3-hydroxypropyl 4-(3,5-di-t-butyl-4-methoxyphenyl)butyrate, 4-hydroxybutyl 4-(3,5-di-t-butyl-4-methoxyphenyl)butyrate, 2-hydroxyethyl 4-(3,5-di-t-butyl-2-methoxyphenyl)butyrate, 2-hydroxyethyl 4-(3-t-butyl-4-ethoxy-5-methylphenyl)butyrate, 3-hydroxypropyl 4-(3-t-butyl-4-ethoxy-5-methylphenyl)butyrate, 4-hydroxybutyl 4-(3-t-butyl-4-ethoxy-5-methylphenyl)butyrate, 2-hydroxyethyl 4-(3,5-di-t-butyl-4-ethoxyphenyl)butyrate, 3-hydroxypropyl 4-(3,5-di-t-butyl-4-ethoxyphenyl)butyrate, and 4-hydroxybutyl 4-(3,5-di-t-butyl-4-ethoxyphenyl)butyrate.

These compounds can be produced, for example, by reacting the corresponding diol with the corresponding carboxylic acid, carboxylate or halide carboxylate.

Examples of the hydroxyl compound (XVII) wherein the connecting group F is represented by the formula (X) include phenyl hydroxyacetate, benzyl hydroxyacetate, phenyl 2-hydroxypropionate, benzyl 2-hydroxypropionate, phenyl 3-hydroxypropionate, benzyl 3-hydroxypropionate, phenyl 2-hydroxy-2-methylpropionate, benzyl 2-hydroxy-2-methylpropionate, phenyl 3-hydroxy-2-methylpropionate, benzyl 3-hydroxy-2-methylpropionate, phenyl 2-hydroxybutyrate, benzyl 2-hydroxybutyrate, phenyl 2-hydroxy-2-methylbutyrate, benzyl 2-hydroxy-2-methylbutyrate, phenyl 2-hydroxy-3-methylbutyrate, benzyl 2-hydroxy-3-methylbutyrate, phenyl 2-ethyl-2-hydroxybutyrate, benzyl 2-ethyl-2-hydroxybutyrate, phenyl 3-hydroxybutyrate, benzyl 3-hydroxybutyrate, phenyl 4-hydroxybutyrate, benzyl 4-hydroxybutyrate, phenyl 2-hydroxy-4-methylpentanoate, benzyl 2-hydroxy-4-methylpentanoate, phenyl 2-hydroxyhexanoate and benzyl 2-hydroxyhexanoate.

Examples of the hydroxy compound (XVII) wherein the connecting group F is represented by the formula (XI) include 2-[N-(3-t-butyl-2-hydroxyphenylmethyl)amino]ethanol, 2-[N-(3-t-butyl-4-hydroxyphenylmethyl)amino]ethanol, 2-(N-(3-t-butyl-2-hydroxy-5-methylphenylmethyl)amino]ethanol, 2-[N-(3,5-di-t-butyl-2-hydroxyphenylmethyl)amino]ethanol, 2-[N-(3-t-butyl-4-hydroxy-5-methylphenylmethyl)amino]ethanol, 2-[N-(3,5-di-t-butyl-4-hydroxyphenylmethyl)amino]ethanol, 2-[N-(2-methyl-3,5-di-t-butyl-4-hydroxyphenylmethyl)amino]ethanol, 2-[N-(3-t-butyl-2-methoxyphenylmethyl)amino]ethanol, 2-[N-(3-t-butyl-4-methoxyphenylmethyl)amino]ethanol, 2-[N-(3-t-butyl-2-methoxy-5-methylphenylmethyl)amino]ethanol, 2-]N-(3,5-di-t-butyl-2-methoxyphenlmethylamino]ethanol, 2-[N-(3-t-butyl-4-methoxy-5-methylphenylmethyl)amino]ethanol, 2-[N-(3,5-di-t-butyl-4-methoxyphenylmethyl)amino]ethanol, 2-[N-(2-methyl-3,5-di-t-butyl-4-methoxyphenylmethyl)amino]ethanol, 2-[N-(3-t-butyl-2-hydroxyphenylmethyl)-N-methylamino]ethanol, 2-[N-( 3-t-butyl-4-hydroxyphenylmethyl)-N-methylamino]ethanol, 2-[N-(3-t-butyl-2-hydroxy-5-methylphenylmethyl)-N-methylamino]ethanol, 2-[N-(3,5-di-t-butyl-2-hydroxyphenyimethyl)-N-methylamino]ethanol, 2-[N-(3-t-butyl-4-hydroxy-5-methylphenylmethyl)-N-methylamino]ethanol, 2-[N-(3,5-di-t-butyl-4-hydroxyphenylmethyl)-N-methylamino]ethanol, 2-[N-(2-methyl-3,5-di-t-butyl-4-hydroxyphenylmethyl-N-methylamino]ethanol, 2-[N-(3-t-butyl-2-hydroxyphenylmethyl)-N-ethylamino]ethanol, 2-[N-(3-t-butyl-4-hydroxyphenylmethyl)-N-ethylamino]ethanol, 2-[N-(3-t-butyl-2-hydroxy-5-methylphenylmethyl)-N-ethylamino]ethanol, 2-[N-(3,5-di-t-butyl-2-hydroxyphenylmethyl)-N-ethylamino]ethanol, 2-[N-(3-t-butyl-4-hydroxy-5-methylphenylmethyl)-N-ethylamino]ethanol, 2-[N-(3,5-di-t-butyl-4-hydroxyphenylmethyl)-N-ethylamino]ethanol, 2-[N-(2-methyl-3,5-di-t-butyl-4-hydroxyphenylmethyl)-N-ethylamino]ethanol, 2-[N-(3-t-butyl-2-hydroxyphenylmethyl)-N-t-butylamino]ethanol, 2-[N-(3-t-butyl-4-hydroxyphenylmethyl)-N-t-butylamino]ethanol, 2-[N-(3-t-butyl-2-hydroxy-5-methylphenylmethyl)-N-t-butylamino]ethanol, 2-[N-(3,5-di-t-butyl-2-hydroxyphenylmethyl)-N-t-butylamino]ethanol, 2-[N-(3-t-butyl-4-hydroxy-5-methylphenylmethyl)-N-t-butylamino]ethanol, 2-[N-(3,5-di-t-butyl-4-hydroxyphenylmethyl)-N-t-butylamino]ethanol, 2-[N-(2-methyl-3,5-di-t-butyl-4-hydroxyphenylmethyl)-N-t-butylamino]ethanol, 3-[N-(3-t-butyl-2-hydroxyphenylmethyl)amino]propanol, 3-[N-(3-t-butyl-4-hydroxyphenylmethyl)amino]propanol, 3-[N-(3-t-butyl-2-hydroxy-5-methylphenylmethyl)amino]propanol, 3-[N-(3,5-di-t-butyl-2-hydroxyphenylmethyl)amino]propanol, 3-[N-(3-t-butyl-4-hydroxy-5-methylphenylmethyl)amino]propanol, 3-[N-(3,5-di-t-butyl-4-hydroxyphenylmethyl)amino]propanol, 3-[N-(2-methyl-3,5-di-t-butyl-4-hydroxyphenylmethyl)amino]propanol, 3-[N-(3-t-butyl-2-hydroxy-5-methylphenylmethyl)-N-methyl-amino]propanol, 3-[N-(3,5-di-t-butyl-2-hydroxyphenylmethyl)-N-methylamino]propanol, 3-[N-(3-t-butyl-4-hydroxy-5-methylphenylmethyl)-N-methylamino]propanol, 3-[N-(3,5-di-t-butyl-4-hydroxyphenylmethyl)-N-methylamino]propanol, 4-[N-(3-t-butyl-2-hydroxyphenylmethyl)amino]butanol, 4-[N-(3-t-butyl-4-hydroxyphenylmethyl)amino]butanol, 4-[N-(3-t-butyl-2-hydroxy-5-methylphenylmethyl)amino]butanol, 4-[N-(3,5-di-t-butyl-2-hydroxyphenylmethyl)amino]butanol, 4-[N-(3-t-butyl-4-hydroxy-5-methylphenylmethyl)amino]butanol, 4-[N-(3,5-di-t-butyl-4-hydroxyphenylmethyl)amino]butanol, 4-[N-(2-methyl-3,5-di-t-butyl-4-hydroxyphenylmethyl)amino]butanol, 4-[N-(3-t-butyl-2-hydroxy-5-methylphenylmethyl)-N-methylamino]butanol, 4-[N-(3,5-di-t-butyl-2-hydroxyphenylmethyl)-N- methylamino]butanol, 4-[N-(3-t-butyl-4-hydroxy-5-methylphenylmethyl)-N-t-methylamino]butanol and 4-[N-(3,5-di-t-butyl-4 -hydroxyphenylmethyl)-N-methylamino]butanol.

When A is methylene, these compounds can be produced, for example, by reacting the corresponding alkanolamine with the corresponding phenol compound and formaldehyde. When A is an alkylene other than methylene, the compounds can be produced by reacting the corresponding alkanolamine with the corresponding halide.

Examples of the hydroxyl compound (XVII) wherein the connecting group F is a group off formula (XII) include N-(2-hydroxyethyl)-2-hydroxy-3-t-butylbenzamide, N-(2-hydroxyethyl)-4-hydroxy-3-t-butylbenzamide, N-(2-hydroxyethyl)-2-hydroxy-3-t-butyl-5-methylbenzamide, N-(2-hydroxyethyl)-4-hydroxy-3-t-butyl-5-methylbenzamide, -N-(2-hydroxyethyl)-2-hydroxy-3,5-di-t-4-butylbenzamide, N-(2-hydroxyethyl)-4-hydroxy-3,5-di-t-butyl-benzamide, N-(2-hydroxyethyl)-3-(2-hydroxy-3-t-butylphenyl)propionamide, N-(2-hydroxyethyl)-3-(4-hydroxy-3-t-butylphenyl)propionamide, N-(2-hydroxyethyl)-3-(2-hydroxy-3-t-butyl-5-methylphenyl)propionamide, N-(2-hydroxyethyl)-3-(4-hydroxy-3-t-butyl-5-methylphenyl)propionamide, N-(2-hydroxyethyl)-3-(2-hydroxy-3,5-di-t-butylphenyl-)propionamide, N-(2-hydroxyethyl)-3-(4-hydroxy-3,5-di-t-butylphenyl)propionamide, N-methyl-N-(2-hydroxyethyl)-3-(2-hydroxy-3-t-butylphenyl)propionamide, N-methyl-N-(2-hydroxyethyl)-3-(4-hydroxy-3-t-butylphenyl)propionamide, N-methyl-N-(2-hydroxyethyl)-3-(2-hydroxy-3-t-butyl-5-methylphenyl)propionamide, N-ethyl-N-(2-hydroxyethyl)-3-(4-hydroxy-3-t-butyl-5-ethylphenyl)propionamide, N-methyl-N-(2-hydroxyethyl)-3-(2-hydroxy-3,5-di-t-butylphenyl)propionamide, N-methyl-N-(2-hydroxyethyl)-3-(4-hydroxy-3,5-di-t-butylphenyl)propionamide, N-ethyl-N-(2-hydroxyethyl)-3-(2-hydroxy-3-t-butylphenyl)propionamide, N-ethyl-N-(2-hydroxyethyl)-3-(4-hydroxy-3-t-butylphenyl)propionamide, N-ethyl-N-(2-hydroxyethyl)-3-(2-hydroxy-3-t-butyl-5-methylphenyl)propionamide, N-ethyl-N-(2-hydroxyethyl)-3-(4-hydroxy-3-t-butyl-5-methylphenyl)propionamide, N-ethyl-N-(2-hydroxyethyl)-3-(2-hydroxy-3,5-di-t-butylphenyl)propionamide, N-ethyl-N-(2-hydroxyethyl)-3-(4-hydroxy-3,5-di-t-butylphenyl)propionamide, N-t-butyl-N-(2-hydroxyethyl)-3-(2-hydroxy-3-t-butylphenyl)propionamide, N-t-butyl-N-(2-hydroxyethyl)-3-(4-hydroxy-3-t-butylphenyl)propionamide, N-t-butyl-N-(2-hydroxyethyl)-3-(2-hydroxy-3-t-butyl-5-methylphenyl)propionamide, N-t-butyl-N-(2-hydroxyethyl)-3-(4-hydroxy-3-t-butyl-5-methylphenyl)propionamide, N-t-butyl-N-(2-hydroxyethyl)-3-(2-hydroxy-3,5-di-t-butylphenyl)propionamide, N-t-butyl-N-(2-hydroxyethyl)-3-(4-hydroxy-3,5-di-t-butylphenyl)propionamide, N-(3-hydroxypropyl)-3-(2-hydroxy-3-t-butylphenyl)propionamide, N-(3-hydroxypropyl)-3-(4-hydroxy-3-t-butylphenyl)propionamide, N-(3-hydroxypropyl)-3-(2-hydroxy-3-t-butyl-5-methylphenyl)propionamide, N-(3-hydroxypropyl)-3-(4-hydroxy-3-t-butyl-5-methylphenyl)propionamide, N-(3-hydroxypropyl)-3-(2-hydroxy-3,5-di-t-butylphenyl)propionamide, N-(3-hydroxypropyl)-3-(4-hydroxy-3,5-di-t-butylphenyl)propionamide, N-(4-hydroxybutyl)-3-(2-hydroxy-3-t-butylphenyl)propionamide, N-(4-hydroxybutyl)-3-(4-hydroxy-3-t-butylphenyl)propionamide, N-(4-hydroxybutyl)-3-(2-hydroxy-3-t-butyl-5-methylphenyl)propionamide, N-(4-hydroxybutyl)-3-(4-hydroxy-3-t-butyl-5-methylphenyl)propionamide, N-(4-hydroxybutyl)-3-(2-hydroxy-3,5-di-t-butylnhenyl)propionamide, N-(4-hydroxybutyl)-3-(4-hydroxy-3,5-di-t-butylphenyl)propionamide, N-(6-hydroxyhexyl)-3-(2-hydroxy-3-t-butylphenyl)prooionamide, N-(l6-hydroxyhexyl)-3-(4-hydroxy-3-t-butylphenyl)propionamide, N-(6-hydroxyhexyl)-3-(2-hydroxy-3-t-butyl-5-methylphenyl)propionamide, N-(6-hydroxyhexyl)-3-(4-hydroxy-3-t-butyl-5-methylphenyl)propionamide, N-(6-hydroxyhexyl)-3-(2-hydroxy-3,5-di-t-butylphenyl)propionamide, N-(6-hydroxyhexyl)-3-(4-hydroxy-3,5-di-t-butylphenyl)propionamide, N-[1-(hydroxymethyl-)-1-methyl-2-hydroxyethyl]-2-hydroxy-3-t-butylbenzamide, N-[1-(hydroxymethyl)-1-methyl-2-hydroxyethyl]-4-hydroxy-3-t-butylbenzamide, N-[1-(hydroxymethyl)-1-methyl-2-hydroxyethyl-2-hydroxy-3-t-butyl-5-methylbenzamide, N-[1-(hydroxymethyl)-1-methyl-2-hydroxyethyl]-4-hydroxy-3-t-butyl-5-methylbenzamide, N-[1-(hydroxymethyl)-1-methyl-2-hydroxyethyl]-2-hydroxy- 3,5-di-t-butylbenzamide, N-[1-(hydroxymethyl)-1-methyl-2-hydroxyethyl]-4-hydroxy-3,5-di-t-butylbenzamide, -N-[1-(hydroxymethyl)-1-methyl-2-hydroxyethyl]-3-(2-hydroxy-3-t-butylphenyl)propionamide, N-[1-(hydroxymethyl)-1-methyl-2-hydroxyethyl]-3-(4-hydroxy-3-t-butylphenyl)propionamide, N-[1-(hydroxymethyl)-1-methyl-2-hydroxyethyl]-3-(2-hydroxy-3-t-butyl-5-methylphenyl)propionamide, N-[1-(hydroxymethyl)-1-methyl-2-hydroxyethyl]-3-(4-hydroxy-3-t-butyl-5-methylphenyl)propionamide, N-[1-(hydroxymethyl)-1-methyl-2-hydroxyethyl]-3-(2-hydroxy-3,5-di-t-butylphenyl)propionamide, N-[1-(hydroxymethyl)-1-methyl-2-hydroxyethyl]-3-(4-hydroxy-3,5-di-t-butylphenyl)propionamide, N-methyl-N-[1-(hydroxymethyl)-1-methyl-2-hydroxyethyl]-3-(2-hydroxy-3-t-butylphenyl)propionamide, N-methyl-N-[1-(hydroxymethyl)-1-methyl-2-hydroxyethyl]-3-(4-hydroxy-3-t-butylphenyl)propionamide, N-methyl-N-[1-(hydroxymethyl)-1-methyl-2-hydroxyethyl]-3-(2-hydroxy-3-t-butyl-5-methylphenyl)propionamide, N-methyl-N-[1-(hydroxymethyl)-1-methyl-2-hydroxyethylyl]-3-(4-hydroxy-3-t-butyl-5-methylphenyl)prooionamide, N-methyl-N-[1-(hydroxymethyl)-1-methyl-2-hydroxyethyl]-3-(2-hydroxy-3,5-di-t-butylphenyl)propionamide, N-methyl-N-[1-(hydroxymethyl)-1-methyl-2-hydroxyethyl]-3-(4-hydroxy-3,5-di-t-butylphenylipropionamide, N-ethyl-N-[1-(hydroxymethyl)-1-methyl-2-hydroxyethyl]-3-(2-hydroxy-3-t-butylphenyl)propionamide, N-ethyl-N-[1 -(hydroxymethyl)-1-methyl-2-hydroxyethyl]-3-(4-hydroxy-3-t-butylphenyl)propionamide, N-ethyl-N-(1-(hydroxymethyl)-1-methyl-2-hydroxyethyl]-3-(2-hydroxy-3-t-butyl-5-methylphenyl)propionamide, N-ethyl-N-[1-(hydroxymethyl)-1-methyl-2-hydroxyethyl]-3-(4-hydroxy-3-t-butyl-5-methylphenyl)propionamide, N-ethyl-N-[1-(hydroxymethyl)-1-methyl-2-hydroxyethyl]-3-(2-hydroxy-3,5-di-t-butylphenyl)propionamide, N-ethyl-N-[1-(hydroxymethyl)-1-methyl-2-hydroxyethyl]-3-(4-hydroxy-3,5-di-t-butylphenyl)propionamide, N-t-butyl-N-[1-(hydroxymethyl)-1-methyl-2-hydroxyethyl]-3-(2-hydroxy-3-t-butylphenyl)propionamide, N-t-butyl-N-[1-(hydroxymethyl)-1-methyl-2-hydroxyethyl]-3-(4-hydroxy-3-t-butylphenyl)propionamide, N-t-butyl-N-[1-(hydroxymethyl)-1-methyl-2-hydroxyethyl]-3-(2-hydroxy-3-t-butyl-5-methylphenyl)propionamide, N-t-butyl-N-[1-(hydroxymethyl)-1-methyl-2-hydroxyethyl]-3-(4-hydroxy-3-t-butyl-5-methylphenyl)propionamide, N-t-butyl-N-[1-(hydroxymethyl)-1-methyl-2-hydroxyethyl]-3-(2-hydroxy-3,5-di-t-butylphenyl)propionamide, N-t-butyl-N-[1-(hydroxymethyl)-1-methyl- 2-hydroxyethyl]-3-(4-hydroxy-3,5-di-t-butylphenyl) propionamide, N-[1-(hydroxymethyl)-1-ethyl-2-hydroxyethyl]-2-hydroxy-3-t-butylbenzamide, N-1-(hydroxymethyl)-1-ethyl-2-hydroxyethyl]1-4-hydroxy-3-t-butylbenzamide, N-[1-(hydroxymethyl)-1-ethyl-2-hydroxyethyl]-2-hydroxy-3-t-butyl-5-methylbenzamide, N-[1-(hydroxymethyl)-2-ethyl-2-hydroxyethyl]-4-hydroxy-3-t-butyl-5-methylbenzamide, N-[1-(hydroxymethyl)-1-ethyl-2 -hydroxyethyl]-2-hydroxy-3,5-di-t-butylbezamide, N-[1-(hydroxymethyl)-1-ethyl-2-hydroxyethyl]-4-hydroxy-3,5-di-t-butylbenzamide, N-[1-(hydroxymethyl)-1-ethyl-2-hydroxyethyl]-3-(2-hydroxy-3-t-butylphenyl) propionamide, N-[1-(hydroxymethyl)-1-ethyl-2-hydroxyethyl]-3-(4-hydroxy-3-t-butylphenyl) propionamide, N-[1-(hydroxymethyl)-1-ethyl-2-hydroxyethyl]-3-(2-hydroxy-3-t-butyl)-1-5-methylphenyl) propionamide, N-[1-(hydroxymethyl)-1-ethyl-2-hydroxyethyl]-3-(4-hydroxy-3-t-butyl-5-methylphenyl) propionamide, N-[1-(hydroxymethyl)-1-ethyl-2-hydroxyethyl]-3-(2-hydroxy-3,5-di-t-butylphenyl) propionamide N-[1-(hydroxymethyl)-1-ethyl-2-hydroxyethyl]-3-(4-hydroxy-3,5-di-t-butylphenyl) propionamide, N-methyl-N-[1-(hydroxymethyl)-1-ethyl-2-hydroxyethyl]-3-(2-hydroxy-3-t-butylphenyl) propionamider N-methyl-N-[1-(hydroxymethyl)-1-ethyl-2-hydroxyethyl]-3-(4-hydroxy-3-t-butylphenyl) propionamide, N-methyl-N-[1-(hydroxymethyl)-1-ethyl-2-hydroxyethyl]-3-(2-hydroxy-3-t-butyl-5-methylphenyl) propionamide, N-methyl-N-[1-(hydroxymethyl)-1-ethyl-2-hydroxyethyl]-3-(4-hydroxy-3-t-butyl-5-methylphenyl) propionamide, N-methyl-N-[1-(hydroxymethyl)-1-ethyl-2-hydroxyethyl]-3-(2-hydroxy-3,5-di-t-butylphenyl) propionamide, N-methyl-N-[1-(hydroxymethyl)-1-ethyl-2-hydroxyethyl]-3-(4-hydroxy-3,5-di-t-butylphenyl) propionamide, N-ethyl-N-(1-(hydroxymethyl))-1-ethyl-2-hydroxyethyl]-3-(2-hydroxy-3 -t-butylphenyl) propionamide, N-ethyl-N-[1-(hydroxymethyl)-1-ethyl-2-hydroxyethyl]-3-(4-hydroxy-3-t-butylphenyl) propionamide, N-ethyl-N-[1-(hydroxymethyl)-1-ethyl-2-hydroxyethyl]-3-(2-hydroxy-3-t-butyl-5-methylphenyl) propionamide, N-ethyl-N-[1-(hydroxymethyl)-1-ethyl-2-hydroxyethyl]-3-(4-hydroxy-3-t-butyl-5-methylphenyl) propionamide, N-ethyl-N-[1-(hydroxymethyl)-1-ethyl-2-hydroxyethyl]-3-(2-hydroxy-3,5-di-t-butylphenyl) propionamide, N-ethyl-N-[1-(hydroxymethyl)-1-ethyl-2-hydroxyethyl]-3-(4-hydroxy-3,5-di-t-butylphenyl) propionamide, N-t-butyl-N-[1-(hydroxymethyl)-1-ethyl-2-hydroxyethyl]-3-(2-hydroxy-3-t-butylphenyl) propionamide, N-t-butyl-N-[1-(hydroxymethyl)-1-ethyl-2-hydroxyethyl]-3-(4-hydroxy-3-t-butylphenyl) propionamide, N-t-butyl-N-[1-(hydroxymethyl)-1-ethyl-2-hydroxyethyl]-3-(2-hydroxy-3-t-butyl-5-methylphenyl) propionamide, N-t-butyl-N-[1-(hydroxymethyl)-1-ethyl-2-hydroxyethyl]-3-(4-hydroxy-3-t-butyl-5-methylphenyl) propionamide, N-t-butyl-N-[1-(hydroxymethyl)-1-ethyl-2-hydroxyethyl]-3-(2-hydroxy-3,5-di-t-butylphenyl) propionamide and N-t-butyl-N-[1-(hydroxymethyl)-1-ethyl-2-hydroxyethyl]-3-(4-hydroxy-3,5-di-t-butylphenyl) propionamide.

These compounds can be produced, for example, by reacting the corresponding aminoalcohol with the corresponding carboxylic acid, carboxylate or halide carboxylate according to the known methods described in USSR Patent No. 1203083 and French Patent No. 2577242.

The pentavalent phosphorus compound of formula (I) can also be produced by oxidizing a corresponding trivalent phosphorus compound, for example, according to methods described in J. Org. Chem.25, 1000(1959). The corresponding trivalent phosphorus compound can be produced, for example, according to methods described in JP-A-5-86084, JP-A-8-41245, JP-A-8-205738, JP-A-8-207445, JP-A-8-246271, JP-A-8-208463, JP-A-8-223779, JP-A-8-222491, JP-A-8-252924, JP-A-8-261653 and JP-A-8-254485.

Specific examples of the pentavalent phosphorus compound of the present invention thus obtained include 3-(3-t-butyl-4-hydroxy-5-methylphenyl)propionic acid 2-[4,8-di-t-butyl-2,10-dimethyl-6-oxo-12H-dibenzo[d,g][1,3,2]dioxaphosphocin-6-yl)oxy]ethyl, 3-(3-t-butyl-4-hydroxy-5-methylphenyl)propionic acid 4-[4,8-di-t-butyl-2,10-dimethyl-6-oxo-12H-dibenzo[d,g][1,3,2]dioxaphosphocin-6-yl)oxylbutyl, 3-(3-t-butyl-4-hydroxy-5-methylphenyl) prop onic acid 5-[4,8-di-t-butyl-2,10-dimethyl-6-oxo-12H-dibenzo[d,g][1,3,2]dioxaphosphocin-6-yl)oxylpentyl, 3-(3-t-butyl-4-hydroxy-5-methylphenyl)propionic acid 8-[4,8-di-t-butyl-2,10-dimethyl-6-oxo-12H-dibenzo[d,g][1,3,2]dioxaphosphocin-6-yl)oxyloctyl, 3-(3-t-butyl-4-hydroxy-5-methylphenyl)propionic acid 2-[2,4,8,10-tetra-t-butyl-6-oxo-12H-dibenzo[d,g][1,3,2]dioxaphosphocin-6-yl)oxy]ethyl, 3-(3-t-butyl-4-hydroxy-5-methylphenyl)propionic acid 4-[2,4,8,10-tetra-t-butyl-6-oxo-12H-dibenzo[d,g][1,3,2]dioxaphosohocin-6-yl)oxy]butyl, 3-(3-t-butyl-4-hydroxy-5-methylphenyl)propionic acid 5-[2,4,8,10-tetra-t-butyl-6-oxo-12H-dibenzo[d,g][1,3,2]dioxaphosphocin-6-yl)oxy]pentyl, 3-(3-t-butyl-4-hydroxy-5-methylphenyl)propionic acid 8-[2,4,8,10-tetra-t-butyl-6-oxo-12H-dibenzo[d,g][1,3,2]dioxaphosphocin-6-yl)oxy]octyl, 3-(3,5-di-t-butylphenyl)propionic acid 2-[2,4,8,10-tetra-t-butyl-6-oxo-12H-dibenzo[d,g][1,3,2]dioxaphosphocin-6-yl)oxy]ethyl, 3-(3-t-butyl-4-hydroxyphenyl)propionic acid 2-[2,4,8,10-tetra-t-butyl-6-oxo-12H-dibenzo[d,g][1,3,2]dioxaphosphocin-6-yl)oxy]ethyl, 3-(3-t-butyl-4-hydroxy-5-methylphenyl)propionic acid 2-[2,4,8,10-tetra-t-butyl-6-oxo-12-methyl-12Hdibenzo[d,g][1,3,2]dioxaphosphocin-6-yloxy]ethyl, 3-(3-t-butyl-4-hydroxy-5-methylphenyl)propionic acid 2-2,4,8,10-tetra-t-butyl-6-oxo-dibenzo[d,f][1,3,2]dioxaphosphepin-6-yl)oxy]ethyl, 3-(3,5-di-t-butyl-4-hydroxyphenyl)propicnic acid 2-[2,4,8,10-tetra-t-butyl-6-oxo-dibenzo[d,f][1,3,2]dioxaphosphepin-6-yl)oxy]ethyl, 3-(3-t-butyl-4-hydroxy-5-methylphenyl)propionic acid 2-[2,4,8,10-tetra-t-butyl-6-oxo-12-methyl-12H-dibenzo[d,g][1,3,2]dioxanhosphocin-6-yl)oxy]ethyl, 3-(3-t-butyl-4-methoxy-5-methylphenyl)propionic acid 2-(2,4,8,10-tetra-t-butyl-6-oxo-12H-dibenzo[d,f][1,3,2]dioxaphosphepin-6-yl)oxy]ethyl, 3-(3,5-di-t-butyl-4-hydroxyphenyl)propionic acid 3-[(6H-6 -oxo-dibenzo[c,e][1,2]oxaphosphoricin-6-yl)oxy]ethyl, 3-phenylpropionic acid 2-[2,4,8,10-tetra-t-butyl-6-oxo-12-methyl-12H-dibenzo[d,g][1,3,2]dioxaphosphocin-6-yl)oxy]ethyl, 2-[2-(4,8-di-t-butyl-2,10-dimethyl-6-oxo-12H-dibenzo[d,g][1,3,2]dioxaphosphocin-6-yl)oxy-3-t-butyl-5-methylbenzyl]-6-t-butyl-4-methylphenol, 2-[2-(2,4,8,10-tetra-t-butyl-6-oxo-12H-dibenzo[d,g][1,3,2]dioxahosphocin-6-yl)oxy-3,5-di-t-butylbenzyl]-4,6-di-t-butylphenol, 2-[1-[2-(4,8-di-t-butyl-2,10-dimethyl-6-oxo-12H-dibenzo[d,g][1,3,2]dioxaphosophocin-6-yl)oxy-3-t-butyl-5-methylphenyl]ethyl]-6-t-butyl-4-methylphenol, 2-[1-[2-(2,4,8,10-tetra-t-butyl-6-oxo-1 2-methyl-12Hdibenzo[d,g][1,3,2]dioxaphosohocin-6-yl)oxy-3,5-di-t-butylphenyl]ethyl]-4,6-di-t-butylphenol, 2-[2-(4,8-di-t-butyl-2,10-di-6-oxo-12H-dibenzo[d,g][1,3,2]dioxaohoshocin-6-yl)oxy-3,5-di-t-butylphenyl]-4,6-di-t-butylphenol, 2-[1-[2-(4,8-di-t-butyl-2,10-dimethyl-6-oxo-12H-dibenzo[d,g]1,3,2]dioxaphosphocin-6-yl)oxy-3,5-di-t-butylphenyl]ethyl]-4,6-di-t-butylphenol, 2-[1-[2-(4,8-di-t-butyl-2,10-dirmethyl-6-oxo-12H-dibenzo[d,g][1,3,2]

dioxaphosphocin-6-yl)oxy-3,5-di-t-pentaphenyl]ethyl]-4,6-di-t-pentylphenol, 2-[2-(2,4,8,10-tetra-t-butyl-6-oxo-12-methyl-12H-dibenzo[d,g][1,3,2]dioxaphosohocin-6-yl)oxy-3-t-butyl-5-methylbenzyl]-6-t-butyl-4-methylphenol, 2-[2-(2,4,8,10-tetra-t-pentyl-6-oxo-12-methyl-12H-dibenzo[d,g][1,3,2]dioxaphosphocin-6-yl)oxy-3-t-butyl-5-methylbenzyl]-6-t-butyl-4-methylphenol, 2-[1-[2-(4,8-di-t-butyl-2,10-dimethyl-6-oxo-12H-dibenzo[d,g][1,3,2]dioxaphosphocin-6-yl)oxy-3-t-butyl-5-methylphenyl]propyl]-6-t-butyl-4-methylphenol, 2-[2-(4,8-di-t-butyl-2,10-di-methyl-6-oxo-12-ethyl-12H-dibenzo[d,g][1,3,2]dioxaphosphocin-6-yl)oxy-3-t-butyl-5-methylbenzyl]-6-t-butyl-4-miethylphenol, 2-[2-(4,8-di-t-butyl-2,10-di-methyl-6-oxo-12-propyl-12H-dibenzo[d,g][1,3,2]dioxaphosphocin-6-yl)oxy-3-t-butyl-5-methylbenzyl]-6-t-butyl-4-methylphenol, 2-[2-(4,8-di-t-butyl-2,10-dimethyl-6-oxo-12-i-propyl-12H-dibenzo[d,g][1,3,2]dioxaphosphocin-6-yl)oxy-3-t-butyl-5-methylbenzyl]-6-t-butyl-4-methylphenol, 2-[2-(2,4,8,10-tetra-t-butyl-6-oxo-dibenzo[d,g][1,3,2]dioxaphosphepin-6-yl)oxy-3-t-butyl-5-methylbenzyl]-6-t-butyl-4-methylphenol, 2-[1-(2,4,8,10-tetra-t-butyl-6-oxo-dibenzo[d,f][1,3,2]dioxaphosphepin-6-yl)oxy-3,5-di-t-butylphenyl]ethyl]-4,6-di-t-butyiphenol, 2-[1-(2,4,8,10-tetra-t-butyl-6-oxo-dibenzo[d,f][1,3,2]dioxaphosphepin-6-yl)oxy-3-t-butyl-5-methylphenyl]ethyl]-6-t-butyl-4-methylphenol, 2-[1-[2-(2,4,8,10-tetra-t-pentyl-6-oxo-1 2-methyl-12Hdibenzo[d,f][1,3,2]dioxaphosophocin-6-yl)oxy-3-t-butyl-5-methylphenyl]ethyl]-6-t-butyl-4-methylphenol, 2-[2-(2,4,8,10-tetra-t-pentyl-6-oxo-12-methyl-12Hdibenzo[d,f][1,3,2]di-oxaphosphocin-6-yl)oxy-3,5-di-t-butylphenyl]-4,6-di-t-butylphenol, 2-[2-(2,4,8,10-tetra-t-butyl- 6-oxo-12-ethyl-12H-dibenzo[d,g][1,3,2]dioxaphosphocin-6-yl)oxy-3,5-di-t-butylphenyl]-4,6-di-t-butylphenol, 3-(3,5-di-t-butyl-4-hydroxyphenyl)-1-[(2,10-dimethyl-4,8-di-t-butyl-6-oxo-12H-dibenzo[d,g][1,3,2]dioxaphosphocin-6-yl)oxy]propane, 3-(3,5-di-t-butyl-4-hydroxyphenyl)-1-[(2,4,8,10-tetra-t-butyl-dibenzo[d,f][1,3,2]dioxaphosphepin-6-yl)oxy]propane, 3-(3,5-di-t-butyl-4-hydroxyphenyl)-1-[(2,4,8,10-tetra-t-pentyl-6-oxo-12-methyl-12H-dibenzo[d,f][1,3,2]dioxaphosphocin-6-yl)oxy]propane, 2,10-dimethyl-4,8-di-t-butyl-6-[3-(3,5-di-t-butyl-4-hydroxyphenyl)propionyloxy]-6-oxo-12H-dibenzo[d,f][1,3,2]dioxaphosphocin, 2,4,8,10-tetra-t-pentyl-6-[3-(3,5-di-t-butyl-4-hydroxyphenyl)propionyloxy]-6-oxo-12-methyl-12H-dibenzo[d,g][1,3,2]dioxaphosphocin, 2,4,8,10-tetra-t-pentyl-6-[3-(3,5-di-t-butyl-4-hydroxyphenyl)propionyloxy]-6-oxo-dibenzo[d,f][1,3,2]dioxaphosphepin, 2,10-dimethyl-4,8-di-t-butyl-6-(3,5-di-t-butyl-4-hydroxyphenylbenzoyloxy)-6-oxo-12H-dibenzo[d,g][1,3,2]dioxaphosphocin, 2,4,8,10-tetra-t-butyl-6-(3,5-di-t-butyl-4-hydroxyphenylbenzoyloxy)-6-oxo-12-methyl-12H-dibenzo[d,g][1,3,2]dioxaphosphocin, 2-(3,5-di-t-butyl-4-hydroxyphenylmethyloxy)-[(4,8-di-t-butyl-2,10-dimethyl-6-oxo-12H-dibenzo[d,g][1,3,2]dioxaphosphocin-6-yl)oxy]ethane, 2 -(3,5-di-t-butyl-4-hydroxyphenylmethyloxy)-[(2,4,8,10-tetra-t-pentyl-6-oxo-12-methyl-12H-dibenzo[d,g][1,3,2]dioxaphosphocin-6-yl)oxy]ethane, [(2,4,8,10-tetra-t-butyl-6-oxo-dibenzo[d,f][1,3,2]dioxaphosphepin-6-yl)oxy]-benzyloxycarboylmethane, [(2,4,8,10-tetra-t-butyl-6-oxo-12H-dibenzo[d,g][1,3,2]dioxaphosphocin-6-yl)oxy]-benzyloxycarboylmethane, 2,10-dimethyl-4,8-di-t-butyl-6-[2-{N-(4-hydroxyl-3,5-t-butylphenyl)methyl-N-methylamino}ethoxy]-6-oxo-12H-dibenzo[d,g][1,3,2]dioxaphosphocin, 2,4,8,10-tetra-t-pentyl-6-[2-{N-(4-hydroxyl-3,5-t-butylphenyl)methyl-N-methylamino}ethoxy]-6-oxo-12-methyl-12H-dibenzo[d,g][1,3,2]dioxaphosphocin, 2,4,8,10-tetra-t-butyl-6-[2-{N-(4-hydroxyl-3,5-t-butylphenyl)methyl-N-methylamino}ethoxy]-6-oxo-dibenzo[d,f][1,3,2]dioxaphosphepin, 2,10-dimethyl-4,8-di-t-butyl-6-[2-{N-(2-hydroxyl-3,5-t-butylphenyl)methyl-N-methylamino}ethoxy]-6-oxo-dibenzo[d,g][1,3,2]dioxaphosphocin, 2,4,8,10-tetra-t-pentyl-6-[2-{N-(2-hydroxyl-3,5-t-butyphenyl)methyl-N-methylamino}ethoxy]-6-oxo-12-methyl-12H-dibenzo[d,g][1,3,2]dioxaphosphocin, 2,4,8,10-tetra-t-butyl-6-[2-{N-(2-hydroxyl-3,5-t-butylphenyl)methyl-N-methylamino}ethoxy]-6-oxo-dibenzo[d,g][1,3,2]dioxaphosphepin, N-(4-hydroxyl-3,5-di-t-butylphenylmethyl)-2,2-bis(2,10dimethyl-4,8-di-t-butyl-6-oxo-12H-dibenzo[d,g][1,3,2]dioxaphosohocin-6-yl-6-oxy)-diethylamine, N-(4-hydroxyl-3,5-di-t-butylphernylmethyl)-2,2-bis(2,4,8,10-tetra-t-pentyl-6-oxo-12H-dibenzo[d,g][1,3,2]dioxaphosphocin-6-yl-6-oxy)-diethylamine, N-(2-hydroxyl-3,5-di-t-butylphenylmethyl)-2,2-bis(2,10-dimethyl-4,8-di-t-butyl-6-oxo-12H-dibenzo[d,g][1,3,2]dioxaphosphocin-6-yl-6-oxy)-diethylamine, N-(2-hydroxyl-3,5-di-t-butylphenylmethyl)-2,2-bis(2,4,8,10-tetra-t-pentyl-6-oxo-12H-dibenzo[d,g][1,3,2]dioxaphosphoci-n-6-yl-6-oxy)-diethylamine, 6-[2-[3-(4-hydroxy-3,5-di-t-butylohenyl)propionamide]ethoxy]-2,10-dimethyl-4,8-di-t-butyl-6-oxo-12H-dibenzo[d,g][1,3,2]dioxaphosphocin, 6-[2-[3-(4-hydroxy-3,5-di-t-butylphenyl)propionamide]ethoxy]-2,4,8,10-tetra-t-pentyl-6-oxo-12-methyl-12Hdibenzo[d,g][1,3,2]dioxaphosphocin, 6-[2-[N-methyl-3-(4-hydroxy-3,5-di-t-butylphenyl)propionamide]ethoxy]-2,10-dimethyl-4,8-di-t-butyl-6-oxo-12H-dibenzo[d,g][1,3,2]dioxaphosphocin, N-(2-hydroxy-3,5-di-t-butylphenylmethyl)-2,2-bis(2,4,8,10-tetra-t-pentyl-6-oxo-12H-dibenzo[d,g][1,3,2]dioxaphosphocin-6-yl-6-oxy)-diethylamine, 3-(3,5-di-t-butyl-4-hydroxyphenyl)propionic acid 2-[(2,4-di-t-butyl-6-oxo-benzo[d][1,3,2]dioxaphosphor-6-yl)oxy]ethyl, 2-[2-[5,5-dimethyl-2-oxo-[1,3,2]dioxaphosphorynan-2-yl]oxy-3-t-butyl-5-methylbenzyl]-6-t-butyl-4-methylphenol, 2-[2-[5,5-dimethyl-2-oxo-[1,3,2]dioxaphosphorynan-2-yl]oxy-3,5-di-t-butylphenyl]-4,6-di-t-butylphenol, 2-[2-[4,5-diphenyl-2-oxo-1,3,2-dioxaphosphoran-2-yl]oxy-3-t-butyl-5-methylbenzyl]-6-t-butyl-4-methylphenol and 2-[1-[2-(4,5-diphenyl-2-oxo-1,3,2-dioxaphosphoran-2-yl)oxy-3,5-di-t-butylphenyl]ethyl]-4,6-di-t-butylphenol.

The hydrolysis resistance of the pentavalent phosphorous compounds (I) of the present invention can be improved by containing an amine, an acid-bonded metal salt and the like.

Examples of the amine include trialkanolamines such as triethanolamine, tripropanolamine and tri-i-propanolamine; dialkanolamines such as diethanolamine, dipropanolamine, di-i-propanolamine, tetraethanolethylenediamine and tetra-i-propanolethylenediamine; monoalkanolamines such as dibutylethanolamine and dibutyl-i-propanolamine; aromatic amines such as 1,3,5-trimethyl-2,4,6,6-triazine; alkylamines such as dibutylamine, piDeridine, 2,2,6,6,-tetramethylpiperIdine and 4-hydroxy-2,2,6,6-tetramethylpiperidine; polyalkylenepolvamines such as hexamethylenetetramine, triethylenediamine, triethylenetetramine and tetraethylenepentamine; and hindered amine photostabilizers described hereinafter.

Furthermore, there can also be used a long-chain aliphatic amine described in JP-A-61-63686, a compound having a steric hindrance amine group described in JP-A-6-329830, a hindered piperidinyl photostabilizer described in JP-A-7-90270 and an organic amine described in JP-A-7-278164.

A proportion of the amine to be used is normally about 0.01 to 25% by weight based on the pentavalent phosphorous compounds of formula (I).

Typical examples of the acid-bonded metal salt include hydrotalcites. Examples of the hydrotalcites include double salt compounds represented by the following formula:

wherein $M^{2+}$ represents Mg, Ca, Sr, Ba, Zn, Pb, Sn and/or Ni; $M^{3+}$ represents Al, B or Bi; n represents a numerical value of 1 to 4; x represents a number of 0 to 0.5; p represents a number of 0 to 2; and $A^{n-}$ represents an anion having a valency or n.

Specific examples of the amino having a valence of n represented by $A^{n-}$ include $OH^-$, $Cl^-$, $Br^-$, $I^-$, $ClO_4^-$, $HCO_3^-$, $C_6H_5COO^-$, $CO_3^{2-}$, $SO^{2-}$, —OOCCOO—, $(CHOHCO)_2^{2-}$, $C_2H_4(COO)_2^{2-}$, $(CH_2COO)_2^{2-}$, $CH_3CHOHCOO$—, $SiO_3^{2-}$, $SiO_4^{4-}$, $Fe(CN)_6^{4-}$, $BO_3^{3-}$, $PO_3^{3-}$ and $HPO_4^{2-}$.

Particularly preferred double salt compounds represented by the above formula include hydrotalcites represented by the following formula:

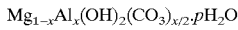

wherein x and p are as defined above.

The hydrotalcites may be natural or synthetic products, and can be used regardless of crystal structure and crystal particle diameter thereof.

Furthermore, an ultrafine zinc oxide described in JP-A-6-329830 and an inorganic compound described in JP-A-7-278164 can also be used.

A proportion of the acid-bonded metal salt to be used is normally about 0.01 to 25% by weight based on the pentavalent phosphorous compound of formula (I).

The pentavalent phosphorous compounds (I) of the present invention are effective for stabilizing an organic material against heat deterioration and oxidization deterioration. Examples of the organic material which can be stabilized by pentavalent phosphorous compounds (I) of the present invention include the following:

(1) polyethylene, for example, high-density polyethylene (HD-PE), low-density polyethylene (LD-PE) and linear low-density polyethylene (LLDPE)
(2) polypropylene
(3) methylpentene polymer
(4) EEA (ethylene/ethyl acrylate copolymer) resin
(5) ethylene/vinyl acetate copolymer resin
(6) polystyrenes, for example, polystyrene, poly(p-methylstyrene) and poly(α-methylstyrene)
(7) As (acrylonitrile/styrene copolymer) resin
(8) ABS (acrylonitrile/butadiene/styrene copolymer) resin
(9) AAS (special acrylic rubber/acrylonitrile/stvrene copolymer) resin
(10) ACS (acrylonitrile/chlorinated polyethylene/styrene copolymer) resin
(11) chlorinated polyethylene, polychloroprene, chlorinated rubber
(12) polyvinyl chloride, polyvinylidene chloride
(13) methacrylic resin
(14) etyhylene/vinyl alcohol copolymer resin
(15) fluororesin
(16) polyacetal
(17) grafted polyphenylene ether resin and polyphenylene sulfide resin
(18) polyurethane
(19) polyamide
(20) polyester resin, for example, polyethylene terephthalate and polybutylene terephthalate
(21) polycarbonate
(22) polyacrylate
(23) polysulfone, polyether ether ketone, polyether sulfone
(24) thermoplastic resin such as aromatic polyester resin, etc.
(25) epoxy resin
(26) diallyl phthalate prepolymer
(27) silicone resin
(28) unsaturated polyester resin
(29) acrylic-modified benzoguanamine resin
(30) benzoguanamine/melamine resin
(31) thermosetting resin such as urea resin, etc.
(32) polybutadiene
(33) 1,2-polybutadiene
(34) polyisoprene
(35) styrene/butadiene copolymer
(36) butadiene/acrylonitrile copolymer
(37) ethylene/propylene copolymer
(38) silicone rubber
(39) epichlorohydrin rubber
(40) acrylic rubber
(41) natural rubber
(42) chlorinated rubber paint
(43) polyester resin paint
(44) urethane resin paint
(45) epoxy resin paint
(46) acrylic resin paint
(47) vinyl resin paint
(48) aminoalkyd resin paint
(49) alkyd resin
(50) nitrocellulose resin paint
(51) oil-based paint
(52) wax, and
(53) lubricating oil.

The organic materials can be stabilized alone or in combination thereof. The organic materials which can be stabilized by pentavalent phosphorous compounds (I) of the present invention are not limited to the organic materials exemplified above Among them, the thermoplastic resin, particularly polyolefin such as polyethylene (e.g. HD-PE, LD-PE, LLDPE, etc.) and polyolefin (e.g. polypropylene, etc.), and the engineering resin such as polyamide, polyethylene terephthalate, polybutylene terephthalate and polycarbonate, are more suitable to be stabilized by pentavalent phosphorous compound (I) of the present invention.

The polyolefins are not specifically limited. For example, they may be those obtained by the radical polymerization or those produced by the polymerization using a catalyst containing a metal of Group IVb, Vb, VIb or VIII of the periodic table. The catalyst containing such a metal may be a metal complex which is coordinated by one or more ligands, for example, oxide which is coordinated by a π or σ bond, halogenated compound, alcolate, ester, aryl and the like, and these complexes may be used as it is, or a base material such as magnesium chloride, titanium chloride, alumina, silicon oxide, etc. may carry the complexes.

As the polyolefin, for example, there are preferably used those produced by using Ziegler-Natta catalyst, TNZ catalyst, metallocene catalyst, Phillips catalyst and the like.

Also the engineering resin is not specifically limited. The polyamide resin may be those which have an amide bond at the-poly merchain and can be molten with heating. For example, they may be produced by any method such as condensation reaction between diamines and dicarboxylic acids, condensation reaction of aminocarboxylic acids and ring opening polymerization of lactams. Typical examples thereof include nylon 66, nylon 69, nylon 610, nylon 612, poly-bis(p-aminocyclohexyl)methanedodecamide, nylon 46, nylon 6, nylon 12 and copolymers (e.g. nylon 66/6 as a copolymer of nylon 66 and nylon 6, nylon 6/12, etc.).

The polyester resin may be those which have an ester bond at the polymer chain and can be molten with heating. Examples thereof include polyester obtained by the polycondensation between dicarboxylic acids and a dihydroxy compound. The polyester may be a homopolyester or a copolyester.

The polycarbonate may be those which have a carbonate bond at the polymer chain and can be molten with heating. Examples thereof include polycarbonate obtained by reacting an aromatic hydroxy compound and/or a small amount of polyhydroxy compound with a carbonate precursor such as phosgene, diphenyl carbonate, etc. in the presence of a solvent, an acid receptor and a molecular weight adjustor, The polycarbonate resin may be straight-chain or branched resin, or may be a copolymer.

When the organic material is stabilized by containing the pentavalent phosphorous compound (I) of the present invention, the pentavalent phosphorous compounds (I) are normally formulated in an amount of about 0.01 to 5 parts by weight, preferably about 0.03 to 3 parts by weight, more preferably about 0.05 to 1 parts by weight, based on 100 parts by weight of the organic material. When the amount is less than 0.01 parts by weight, the stabilizing effect is not sufficient, necessarily. On the other hand, even when the amount exceeds 5 parts by weight, the improvement of the effect corresponding to the amount is not obtained and it is economically disadvantageous.

When the pentavalent phosphorous compounds (I) of the present invention are contained in the organic material, if necessary, there can also be contained other additives such as phenol antioxidant, sulfur antioxidant, phosphorous antioxidant, ultraviolet absorber, photostabilizer, peroxide scavenger, polyamide stabilizer, hydroxylamine, lubricant, plasticizer, flame retardant, nucleating agent, metal inactivating agent, antistatic agent, pigment, filler, pigment, antiblocking agent, surfactant, processing aid, foaming agent, emulsifier, brightener, calcium stearate, neutralizing agent (e.g. hydrotalcite, etc.), coloring modifier (e.g. 9,10-dihydro-oxa-10-phosphophenanthrene-10-oxide, etc.) and co-stabilizer (e.g. benzofurans, indolines, etc. described in U.S. Pat. No. 4,325,853, U.S. Pat. No. 4,338,244, U.S. Pat. No. 5,175,312, U.S. Pat. No. 5,216,053, U.S. Pat. No. 5,252,643 and U.S. Pat. No. 4,316,611, DE-A-4,316,622 and 4,316,876, and EP-A-589,839 and 591,102). These additives can be formulated together with the pentavalent phosphorous compounds (I), and also be formulated in the stage other than the stage where the pentavalent phosphorous compounds (I) are formulated.

Examples of the phenol antioxidant include the followings.

(1) Examples of alkylated monophenol 2,6-di-t-butyl-4-methylphenol, 2,4,6-tri-t-butylphenol, 2,6-di-t-butyl-4-butylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6'-(1'-methylheptadecyl-1'-yl)phenol, 2,4-dimethyl-6-(1'-methyltridecyl-1'-yl)phenol and a mixture thereof.

(2) Examples of alkylthiomethylphenol 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and a mixture thereof (3) Examples of hydroquinone and alkylated hydroquinone 2,6-di-t-butyl-4-methoxyphenol, 2,5-di-t-butylhydroaquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-di-t-butyl-4-hydroxyphenyl)adipate and a mixture thereof (4) Examples of tocopherol α-tocopnerol, β-tocopherol, γtocopherol, δ-tocopherol and a mixture thereof (5) Examples of hydroxylated thiodiphenyl ether 2,2'-thiobis(6-t-butylphenol), 2,2'-thiobis(4-methyl-6-t-butylphenol), 2,2'-thiobis(4-octylphenol), 4,4'-thiobis (3-methyl-6-t-butylphenol), 4,4'-thiols(2-methyl-6-t-butylphenol), 4,4'-thiobis(3,6-di-t-amylphenol), 4,4'-(2,6-dimethyl-4-hydroxyphenyl)disulfide and the like (6) Examples of alkylidenebisphenol and derivative thereof 2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol)], 2,2'-methylenebis(4-methyl-6-cyclohexylphenol), 2,2'-methylenebis(4-methyl-6-nonylphenol), 2,2'-methylenebis(4,6-di-t-butylphenol)], 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(6-t-butyl-2-methylphenol)4,4'-methylenebis(2,6-di-t-butylphenol), 4,4'-butylidenebis(3-methyl-6-t-butylphenol), 1,1-bis (4-hydroxyphenyl)cyclohexane, 1,1-bis(5-t-butyl-4-hydroxy-2-methylphenyl)butane, 2,6-bis[3-t-butyl-5-methyl-2-hydroxybenzyl)-4-methylphenol, 1,1,3-tris (5-t-butyl-4-hydroxy-2-methylphenyl)butane, 1,1-bis (5-t-butyl-4-hydroxy-2-methylphenyl)-3-n-dodecylmercaptobutane, bis[3,3-bis-3'-t-butyl-4'-hydroxyphenyl)butyrate], bis(3-t-butyl-4-hydroxy-5-methylphenyl)dicyclopentadiene, bis[2-(3'-t-butyl-21-hydroxy-5'-methylbenzyl)-6-t-butyl-4-methylphenyl] terephthalate, 1,1-bis(3,5-dimethyl-2-hydroxyphenyl) butane, 2,2-bis(3,5-di-t-butyl-4-hydroxyphenyl) propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate and a mixture thereof.

(7) Examples of O-, N- and S-benzyl derivative 3,5,3',5'-tetra-t-butyl-4,4'-dihydroxydibenzyl ether, octadodecyl-4-hydroxy-3,5-dimethylbenzylmercapto acetate, tris(3,5-di-t-butyl-4-hydroxybenzyl)amine, bis (4-t-butyl-3-hydroxy-2,6-dimethylbenzyl) dithioterephthalate, bis(3,5-di-t-butyl-4-hydroxybenzyl)sulfide, isooctyl-3,5-di-t-butyl-4-hydroxybenzylmercapto acetate and a mixture thereof (8) Examples of hydroxybenzylated malonate derivative dioctadecyl-2,2-bis(3,5-di-t-butyl-2-hydroxybenzyl) malonate, dioctadecyl-2-(3-t-butyl-4-hydroxy-5- methylbenzyl)malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate and a mixture thereof (9) Examples of aromatic hydroxybenzyl derivative 1,3,5-trimethyl-2,4,6-tris(3,5-di-t-butyl-4-hydroxybenzyl)benzene, 1,4-bis(3,5-di-t-butyl-4-hydroxybenzyl)-2,3,5,6-tetramethylbenzene, 2,4,6-tris(3,5-t-butyl-4-hydroxybenzyl)phenol and a mixture thereof

(10) Examples of triazine derivative 2,4-bis(n-octylthio)-6-(4-hydroxy-3,5-di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-hydroxy)-1,3,5-triazine, tris(4-t-butyl-3-hydroxy-2,6-dimethylbenzyl isocyanurate, tris(3,5-di-t-butyl-4-hydroxybenzyl)isocyanurate, 2,4,6-tris(3,5-di-t-butyl-4 -hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'- di-t-butyl-4'-hydroxycinnamoyloxy)ethyl] isocyanurate and a mixture thereof

(11) Examples of benzyl phosphonate derivative dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonic acid monoester and a mixture thereof

(12) Examples of acylaminophenol derivative anilide 4-hydroxylaurate, anilide 4-hydroxystearate, octyl-N-(3,5-di-t-butyl-4-hydroxyphenyl)carbanate and a mixture thereof

(13) Ester of β-(3,5-di-t-butyl-4-hydroxyphenyl) propionic acid and the following monohydric or polyhydric alcohol:

methanol, ethanol, octanol, octadecanol, ethylene glycol, 1,3-propanediol, 1,4-butanedlol, 1,6-hexanediol, 1,9-nonanediol, neopentyl glycol, diethylene glycol, thioethylene glycol, spiro glycol, triethylene glycol, pentaerythrltol, tris(hydroxyethyl-)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(14) Ester of β-(5-t-butyl-4-hydroxy-3-methylphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(15) Ester of β-(3,5-dicyclohexyl-4-hydroxyphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(16) Ester of 3,5-t-butyl-4-hydroxyphenylacetic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(17) Examples of amide of β-(3,5-di-t-butyl-4-hydroxyphenyl)propionic acid and the following amine:

N,N'-bis[3-(3',5'-di-t-butyl-4'-hydroxyphenyl)propionyl] hydrazine, N,N'-bis[3-(3',5'-di-t-butyl-4'-hydroxyphenyl propionyl]hexamethylenediamine, N,N'-bis[3-(3',5'-di-t-butyl-4'-hydroxyphenyl) propionyl]trimethylenediamine and a mixture thereof Examples of the sulfur antioxidant include the followings:

dilauryl 3,3'-thiodipropionate, tridecyl 3,3'-thiodipropionate, dimyristyl 3,3'-thiodipropionate, distearyl 3,3'-thiodipropionate, lauryl stearyl 3,3'-thiodipropionate and neopentanetetraylkis(3-lauryl thiopropionate).

Examples of the phosphorous antioxidant include the followings:

triphenyl phosphite, tris(nonylphenyl)phosphlte, tris(2,4-di-t-butylphenyl)phosphite, trilauryl phosphite. trioctadecyl phosphite, distearyl pentaerythritol diphosphite, diisodecyl pentaerythritol diphosphite, bis(2,4-di-t-butylphenyl)pentaerythritol diphosphite, bis(2,4-di-t-butyl-6-methylphenyl)pentaerythritol diphosphite, bis (2,4-di-t-butyl-6-methylphenyl)pentaerythritol diphosphite, bis(2,6-di-t-butyl-4-methylphenyl) pentaerythritol diphosphite, bis(2,4,6-tri-t-butylphenyl) pentaerythritol diphosphate, tristearyl sorbitol triphosphite, tetrakis(2,4-di-t-butylphenyl)-4,4'-diphenylene diphosphite, 2,2'-methylenebis(4,6-di-t-butylphenyl)2-ethylhexyl phosphite, 2,2'-ethylidenebis (4,6-di-t-butylphenyl)fluoro phosphite, bis(2,4-di-t-butyl-6-methylphenyl)ethyl phosphite, bis(2,4-di-t-butyl-6-methylphenyl)methyl phosphite, (2,4,6-tri-t-butylphenyl)-5-ethyl-5-butyl-1,3,2-oxaphosphorinane, 2,2',2"-nitrilo[triethyl-tris(3,3',5,5'-tetra-t-butyl-1,1'-bipohenyl-2,2'-diyl)phosphite and a mixture thereof Examples of the ultraviolet absorber include the followings:

(1) Examples of salicylate derivative phenyl salicylate, 4-t-butylphenyl salicylate, 2,4-di-t-butylphenyl 3',5'-di-t-butyl-4'-hydroxybenzoate, 4-t-octylphenyl salicylate, bis(4-t-butylbenzoyl)resorcinol, benzoylresorcinol, hexadecyl 3',5'-di-t-butyl-4'-hydroxybenzoate, octadecyl 3',5'-di-t-butyl-4'-hydroxybenzoate, 2-methyl-4,6-di-t-butylphenyl 3',5'-di-t-butyl-4'-hydroxybenzoate and a mixture thereof (2) Examples of 2-hydroxybenzophenone derivative 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2- methoxyphenyl)methane, 2,2',4,4'-tetrahydroxybenzophenone and a mixture thereof (3) Examples of 2-(2'-hydroxyphenyl)benzotriazole 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxypheny)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl-5'-[2-(2-ethylhexyloxy)carbonylethyl]-2'-hydroxyphenyl]-5-chlorobenzotriazole, 2-[3'-t-butyl-2'-hydroxy-5'-(2-methoxycarbonylethyl)phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl] benzotriazole, 2-[3'-t-butyl-2'-hydroxy-5'-[2-(2-ethylhexyloxy)carbonylethyl]phenyl]benzotriazole, 2-[2-hydroxy-3-(3,4,5,6-tetrahydrophthalimidemethyl)-5-methylphenyl] benzotriazole, 2-(3',5'-di-t-butyl-2-hydroxyphenyl)-5-chlorobenzotriazole, mixture of 2-(3'-dodecyl-2'-hydroxy-5'-methylphenyl)benzotriazole and 2-[3'-t-butyl-2'-hydroxy-5'-(2-isooctyloxycarbonylethyl)phenyl]benzotriazole, 2,2'-methylenebis[6-(2H-benzotriazol-2-yl)-4-(1,1,3,3-tetramethylbutyl)phenol, 2,2'-methylenebis[4-t-butyl-6-(2H-benzotriazol-2-yl)phenol], condensate of poly(3-11)(ethylene glycol) and 2-[3'-t-butyl-2'-hydroxy-5'-(2-methoxycarbonylethyl)phenyl]benzotriazole, condensate of poly(3-11)(ethylene glycol) and methyl 3-[3-(2H-benzotriazol-2-yl -5-t-butyl-4-hydroxyphenyl]propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl] propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenylpropionic acid and a mixture thereof.

Examples of the pthotostabilizer include the followings.

(1) Examples of hindered amine photostabilizer bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(-N-octoxy-2,2,6,6-tetramethyl-4-piperidyl)sebacate, bis(N-benzyloxy-2,2,6,6-tetramethyl-4-piper4idyl)sebacate, bis(N-cyclohexyloxy-2,2,6,6-tetramethyl-4-piperidyl)sebacate, bis(1,2.2,6,6-pentamethyl-4-piperidyl) 2-(3,5-di-t-butyl-4-hydroxybenzyl)-2-butylmalonate, bis(1-acrolyl-2,2,6,6-tetramethyl-4 -piperidyl) 2,2-bis(3,5-di-t-butyl-4-hydroxybenzyl)-2-butylmalonate, bis(1,2,2,6,6-penatmethyl-4-piperidyl decanedioate, 2,2,6,6-tetramethyl-4-piperidyl methacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl)propionamide, tetarkis(2,2,6,6-tetramethyl-4-piperidyl) 1,2,3,4-butanetera carboxylate, tetrakis(1,2,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-butanetetracarboxylic acid and 1,2,2,6,6-pentamethyl-4-piperidinol and 3,9-bis(2-hydroxy-1,1-dimethylethyl)-2,4,8,10-tetraoxaspiro[5.5]undecanel mixed esterified product of 1,2,3,4-butanetetracarboxylic acid and 2,2,6,6-tetarmethyl-4-piperidinol and 3,9-bis(2-hydroxy-1,1-dimethylethyl)-2,4,8,10-tetraoxaspiro [5,5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino)hexamethylene ((2,2,6,6-tetramethyl-4-piperidyl)imino)], poly[(6-(1 3,3 -tetramethylbutyl)imino-1,3,5-triazin-2,4-diyl ((2,2,6,6-tetramethyl-4-piperidyl)imino)hexamethylene ((2,2,6,6-tetramethyl-4-piperidyl)imino)], polycondensate of N,N'-bis(2,2,6,6-tetramethyl-4-piperidyl) hexamethylenediamine and 1,2-bromoethane, N,N',4,7-tetrakis[4,6-bis(N-butyl-N-(2,2,6,6-tetramethyl-4-piperidyl)amino)-1,3,5-triazin-2-yl]-4,7-diazadecane-1,10 diamine, N,N',4-tris[4,6-bis(N-butyl-N-(2,2,6,6-tetramethyl-4-piperidyl)amino)-1,3,5-triazin-2-yl]-4,7-diazadecane-1,10 diamine, N,N',4,7-tetrakis[4,6-bis(N-butyl-N-(1,2,2,6,6-pentamethyl-4-piperidyl)amino)-1,3,5-triazin-2-yl]-4,7-diazadecane- [1,10 diamine, N,N',4-tris[4,6-bis(N-butyl-N-(1,2,2,6,6-pentamethyl-4-piperidyl)amino)-1,3,5-triazin-2-yl]-4,7-diazadecane-1,10 diamine and a mixture thereof (2) Examples of acrylate photostabilizer ethyl α-cyano-β,β-diphenylacrylate, isooctyl α-cyano-β,β-diphenylacrylate, methyl α-carbomethoxycinnamate, methyl α-cyano-β-methyl-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline and a mixture thereof (3) Examples of nickel photostabilizer nickel complex of 2,2'-thiobis-[4-(1,1,3,3-tetramethylbutyl)phenol], nickel dibutyldithiocarbamate, nickel salt of monoalkyl ester, nickel complex of ketoxime and a mixture thereof (4) Examples of oxamide photostabilizer 4,4'-dioctyloxyoxanilide, 2,2'-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-5-t-butyl-2'-ethoxyanilide, 2-ethoxy-5,4'-di-t-butyl-2'-ethyloxanilide and a mixture thereof (5) Examples of 2-(2-hydroxyphenyl)-1,3,5-triazine photostabilzer 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(4-methylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxyphenyl)-4,6-bis(2,4-dimethylphenyl)-1,3,5-triazine and a mixture thereof.

Examples of the metal inactivating agent include the followings:

N,N'-diphenyloxamide, N-salicylal-N'-salicyloylhydrazine, N,N'-bis(salicyloyl)hydrazine, N,N'-bis(3,5-di-t-butyl-4-hydroxyphenylzropionyl) hydrazine, 3-salicyloylamino-1,2,4-triazole, bis(benzylidene)oxalyl dihydrazide, oxalinide, isophthaloyl dihydrazide, sebacoylbisphenyl hydrazide, N,N'-bis(salicyloyl)thiopropionyl dihydrazide and a mixture thereof.

Examples of the peroxide scavenger include ester of β-thiodipropionic acid, mercaptobenzoimidazole, zinc salt of 2-mercaptobenzoimidazole, zinc salt of dibutyldithiocarbamic acid, dioctadecyl disulfide, pentaerythritol tetrakis (β-dodecylmercapto)propionate and a mixture thereof.

Examples of the polyamide stabilizer include copper or divalent manganese salt of iodide or phosphorous compound and a mixture thereof.

Examples of the hydroxyamine include N,N-dibenzylhydroxyamine, N,N-diethylhydroxyamine, N,N-dioctylhydroxyamine, N,N-dilaurylhydroxyamine, N,N-ditetradecylhydroxyamine, N,N-dihexadecylhydroxyamine, N,N-dioctadecylhydroxyamine, N,N-dibenzylhydroxyamine, N,N-dibenzylhydroxyamine, N-hexadecyl-N-octadecylhydroxyamine, N-heptadecyl-N-octadecylhydroxyamine and a mixture thereof.

Examples of the neutralizing agent include calcium stearate, zinc stearate, magnesium stearate, hydrotalcite (basic magnesium aluminum hydroxycarbonate hydride), melamine, amine, polyamide, polyurethane and a mixture thereof.

Examples of the lubricant include aliphatic hydrocarbon (e.g. paraffin, wax, etc.), higher aliphatic acid having 8 to 22 carbon atoms, higher aliphatic acid (having 8 to 22 carbon atoms) metal (Al, Ca, Mg, Zn) salt, aliphatic alcohol having 8 to 22 carbon atoms, polyglycol, ester of higher fatty acid having 4 to 22 carbon atoms and aliphatic monohydric alcohol having 4 to 18 carbon atoms, higher aliphatic amide having 8 to 22 carbon atoms, silicone oil, rosin derivative and the like.

Examples of the nucleating agent include the followings: sodium 2,2'-methylenebis(4,6-di-t-butylphenyl) phosphate, [phosphoric acid-2,2'-methylenebis(4,6-di-t-butylphenyl))dihydroxyaluminum, bis[phosphoric acid-2,2'-methylenebis(4,6-di-t-butylphenyl)] dihydroxyaluminum, tris[phosphoric acid-2,2'-methylenebis(4,6-di-t-butylphenyl)]aluminum, sodium bis(4,6-di-t-butylphenyl)phosphate, benzoic acid metal salt such as sodium benzoate, aluminum p-t-butylbenzoate, 1,3:2,4-bis(O-benzylidene)sorbitol, 1,3:2,4-bis(O-ethylbenzylidene)sorbitol, 1,3:2,4-bis(O-methylbenzylidene)sorbitol, 1,3-O-3,4-dimethylbenzylidene-2,4-O-benzylidenesorbitol, 1,3-O-benzylidene-2,4-0-3,4-dimethylbenzylidene sorbitol, 1,3:2,4-bis(O-3,4-dimethylbenzylidene) sorbitol, 1,3-O-p-chlorobenzylidene-2,4-O-3,4-4-dimethylbenzylidene sorbitol, 1,3-O-3,4-dimethylbenzylidene-2,4-O-p-chlorobenzylidene sorbitol, 1,3:2,4-bis(O-p-chlorobenzylidene)sorbitol and a mixture thereof.

Examples of the filler include calcium carbonate, silicate, glass fiber, asbestos, talc, kaoline, mica, barium sulfate, carbon black, carbon fiber, zeolite and a mixture thereof.

Among these additives above, phenol antioxidant, phosphorous antioxidant, ultraviolet absorber, hindered amine photostabilizer, peroxide scaveneger and neutralizing agent are preferably used.

Examples of the particularly preferred phenol antioxidant include the following compounds, and they may be used in combination of the two or more:

2,6-di-t-butyl-4-methylphenol, 2,4,6-tri-t-butylphenol, 2,4-dioctylthi.omethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis[4-ethyl-6-t-butylphenol), 2,2'-methylenebis(4-ethyl-6-(α-methylcyclohexyl)phenol], 2,2'-methylenebis(4-methyl-6-cyclohexylphenol), 2,2'-methylenebis(4,6-di-t-butylphenol), 2,2'-ethylidenebis (4,6-di-t-butylphenol), 4,4'-methylenebis(6-t-butyl-2-methylphenol),4,4'-methylenebis(2,6-di-t-butylphenol), 4,4'-butylidenebis(3-methyl-6-t-butylphenol), 1,1'-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol, bis[3,3-bis-3'-t-butyl-4'-hydroxyphenyl)butyrate], 2-t-butyl-6-(3'-L-t-butyl-5'-methyl-2'-hydroxybenzyl)-4-methyylphenyl acrylate, 2,4-di-t-pentyl-6-[1-(2-hydroxy-3,5-di-t-pentylphenyl) ethyl]phenyl acrylate, 2,4,6 -tris(3,5-di-t-butyl-4-phneoxy)-1,3,5-triazine, tris(4-t-butyl-3-hydroxy-2,6-dimethylbenzyl)isocyanurate, tris(3,5-di-t-butyl-4-hydroxybenzyl)isocyanurate, tris[2-(3',5'-di-t-butyl-4'-hydroxycinnamoyloxy)ethyl]isocyanurate, diethyl-3,5-di-t-butyl-4-hydroxybenzyl phosphonate, di-n-octadecyl-3,5-di-t-butyl-4-hydroxybenzyl phosphonate, calcium salt of 3,5-di-t-butyl-4-hydroxybenzylphosphonic acid monoester, n-octadecyl 3-(3,5-di-t-butyl-4-hydroxyphenyl)propionate, neopentanetetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyll-4-hydroxy-3-methylcinnamate),3,9-bis[2-(3-(3-t-butyl-4-hydroxy-5-methylphenyl)propionyloxy)-1,1-dimethylethyl]-2,4,8,10-tetraoxaspiro [5.5]undecane, N,N'-bis[3-(3',5'-di-t-butyl-4'-hydroxyphenyl) propionyl]hydrazine and N,N'-bis[3-(3',5'-di-t-butyl-4'-hydroxyphenyl-)propionyl]hexamethylenediamine.

Examples of the particularly preferred phosphorous antioxidant include the followings, and they may be used in combination of the two or more:

tris(nonylphenyl)phosphite, tris(2,4-di-t-butylphenyl) phosphite, distearyl pentaerythritol diphosphite, bis(2, 4-di-t-butylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, tetrakis(2,4-di-t-butylphenyl)-4,4'-diphenylenediphosphite, 2,2'-methylenebis(4,6-di-t-butylphenyl) 2-ethylhexyl phosphite, 2,2'-ethylidenebis (4,6-di-t-butylphenyl)fluorophosphite, bis(2,4-di-t-butyl-6-methylphenyl)ethylphosphite, 2-(2,4,6-tri-t-butylphenyl)-5-ethyl-5-butyl-1,3,2-oxaphosphorinane and 2,2',2"-nitrilo[triethyl tris(3,3',5,5'-tetra-t-butyl-1, 1'-biphenyl-2,2'-diyl)phosphite.

Examples of the particularly preferred ultraviolet absorber include the followings, and two or more kinds of them can be used.

phenyl salicylate, 4-t-butylphenyl salicylate, 2,4-di-t-butylphenyl 3',5'-dl-t-butyl-4'-hydroxybenzoate, 4-t-octylphenyl salycilate, 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2'4,4'- tetrahydroxybenzophenone, 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole and2-[2'-hydroxy-3',5'-bis(α, α-dimethylbenzyl)phenyl]-2H-benzotriazole.

Examples of the particularly preferred photostabilizer include the followings, and two or more kinds of them can be used.

bis(2,2,6,6-tetramethyl-4-piperidyl)sebacate, bis(1,2,2,6,6-pentamethyl-4-piperidyl)sebacate, bis(N-octoxy-2,2,6,6-pentamethyl-4-piperidyl)sebacate, bis(N-octoxy-2,2,6,6-pentamethyl-4-piperi-dyl)sebacate, bis(N-benzyloxy-2,2,6,6-tetarmethyl-4-piperidyl)sebacate, bis(N-cyclohexyloxy-2,2,6,6-tetramethyl-4-piperidyl)sebacate, bis(1,2,2,6,6-pentamethyl.-4-piperidyl) 2-(3,5-di-t-butyl-4-hydroxybenzyl)-2-butylmalonate, bis(1-acryloyl-2,2,6,6-tetramethyl-4-piperidyl) 2,2-bis(3,5-di-t-butyl-4-hydroxybenzyl)-2-butylmalonate, bls(2,2,6,6-tetramethyl-4-piperidyl)succinate, 2,2,6,6-tetramethyl-4-piperidyl methacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetarmethyl-4-piperidyl)propionamide, tetrakis(2,2,6,6-tetramethyl-4-piperidyl) 1,2,3,4-butanetetracarboxylate. tetrakis(1,2,6,6-pentamethyl-4-piperidyl) 1,2,3,4-butanetetracarboxylate, mixed esterified product of 1,2,3,4-butanetetracarboxylic acid and 1,2,2,6,6 -pentamethyl-4-piperidinol and 1-tridecanol, mixed esterified product of 1,2,3,4-butanetetracarboxylic acid and 2,2,6,6-tetramethyl-4-pioeridinol and 1-tridecanol, mixed esterified product of 1,2,3,4-tetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis(2-hydroxy-1,1-dimethylethyyl)-2,4,8,10-tetraoxaspiro[5.5]undecane, -polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl) imino)hexamethylene ((2,2,6,6-tetramethyl-4-piperidyl)imino)] and poly[(6-(1,1,3,3-tetramethylbutyl)-1,3,5-triazin-2,4-diyl ((2,2,6,6-tetramethyl-4-piperidyl)imino)hexamethylene ((2,2,6,6-tetra.methyl-4-pioperidyl)imino)].

For formulating the pentavalent phosphorous compounds (I) and optionally used other additives in the organic material, known all methods and devices for obtaining a homogeneous mixture can be used. For example, when the organic material is a solid polymer, the pentavalent phosphorous compounds (I) and other additives can be directly dry-blended in the solid polymer, or the pentavalent phosphorous compounds (II and other additives can also be formulated in the solid polymer in the form of a masterbatch. When the organic material is a liquid polymer, the pentavalent phosphorous compounds (I) and other additives can be formulated in the polymer solution during or immediately after polymerization in the form of a solution or a dispersion. On the other hand, when the organic material is a liquid such as oil, the pentavalent phosphorous compounds (I) and other additives can also be dissolved by direct addition, or the nentavalent phosphorous compounds (I) and other additives can also be added in the form of a solution or dispersion in a liquid medium.

The pentavalent phosphorous compounds (I) of the present invention have excellent performance as a stabilizer for various organic materials such as thermoplastic resin (e.g. polyolefin, etc.), and the organic material containing this compound is stable to heat and oxidization on their production, processing and use. Therefore, high-quality product can be obtained.

A pentavalent phosphorus compound and method of producing and using the same are disclosed in priority documents Application No. 08-318,281 filed in Japan on Nov. 28, 1996 and Application No. 09-171,858 filed in Japan on Jun. 27, 1997, the complete disclosures of both of which are incorporated herein by reference.

The following Examples further illustrate the present invention in detail but are not to be construed to limit the scope thereof.

EXAMPLE 1

Production of 3-(3,5-di-t-butyl-4-hydroxyphenyl) propionic acid 2-[4,8-di-t-butyl-2,10-dimethyl-6-oxo-12H-dibenzo[d,g][1,3,2]dioxaphosphocin-6-yl) oxy]ethyl (compound 1).

Into a flask equipped with a thermostat, stirrer and cooling tube were charged 13.6 g of 2,2-methylenebis-(6 -t-butyl-4-methylphenol), 130 ml of toluene and 20 ml of tetrahydrofuran under nitrogen flow, and, then, 8.2 g of triethylamine and 2.0 g of 4-dimethylaminopyridine were added thereto with stirring. Subsequently, after adding 6.1 g of phosphorus oxychloride, the resulting solution was kept at room temperature for 24 hours.

Then, 50 ml of toluene and 12.9 g of 3-(3,5-di-t-butyl-4-hydroxyphenyl)propionic acid 2-hydroxyethyl were added to the solution, and, then, 4.0 g of triethylamine was added. After keeping the resulting solution at 80° C. for 4 hours, the solution was cooled to room temperature, and the resulted triethylamine hydrochloride was filtered and the filtrate was washed. The filtrate and the washings were combined and concentrated, and then, the residue was purified by silica gel column chromatography to obtain 23.7 g of a white crystal.

FD-MS: m/z 706 m.p. 68° C.

$^1$H-NMR (CDCl$_3$) 1.40 (s, 18H), 1.43 (s, 18H), 2.27 (s, 6H), 2.64 (t, 2H), 2.89 (t, 2H), 4.42 (m, 2H), 4.60 (m, 2H), 5.09 (s, 1H), 6.98 (d, 2H), 7.00 (d, 2H), 7.04 (2, 2H)

$^-$P-NMR (CDCl$_3$) −12.2 ppm (s)

EXAMPLE 2

Production of 2,4,8,10-tetra-t-butyl-6-[3-(3,5-di-t-butylphenyl)-3,3-dimethylpropionyloxy]-6-oxo-12H-dibenzo[d,g][1,3,2]dioxaphosphocin (compound 2)

Into a flask equipped with a thermometer, stirrer and cooling tube were charged 3.5 g of 2,2-methylenebis-(4,6-di-t-butylphenol) and 100 ml of toluene under nitrogen flow, and, then, 1.1 g of phosphorus trichloride was added with stirring. Subsequently, 1.8 g of triethylamine was added there to and there sulting solution waskept at 80° C. for 14 hours. After cooling to room temperature, 50 ml of toluene and 3.5 g of 3-(3,5-di-t-butyl-4-hydroxyphenyl)-3,3-dimethylpropionic acid were added. After adding 0.9 g of triethylamine, the resulting solution was kept at 80° C. for 8 hours.

Then, after cooling to room temperature, 1.2 g of cumene hydroperoxide was added to the solution and the mixture was stirred for 2 hours. The resulted triethylamine hydrochloride was filtered and the filter cake was washed. The filtrate and the washings were combined and concentrated, and then, the residue was purified by silica gel column chromatography to obtain 3.2 g of a white crystal.

FD-MS: m/z 760 m.p. 188° C.

$^1$H-NMR (CDCl$_3$) 1.25 (s, 18H), 1.28 (s, 18H), 1.44 (s, 18H), 1.68 (s, 6H), 4.0~4.1 (br, 2H), 5.19 (s, 1H), 7.15 (d, 2H), 7.22 (s, 2H), 7.23 (d, 2H)

$^{31}$P-NMR (CDCl$_3$) −19.0 ppm (s)

EXAMPLE 3

Heat Stability Test of Linear Low Density Polyethylene

[Blending Formulation]

| | |
|---|---|
| Unstabilized linear low-density polyethylene | 100 |
| Hydrotalcite | 0.1 |
| Test compound | 0.15 |
| | (parts by weight) |

C-1: compound-1(produced in Example 1)
C-2: compound-2 (produced in Example 2)
P-1: 3,5-di-t-butyl-4-hydroxybenzylphosphonate-diethyl ester
P-2: 2,4,8,10-tetra-t-butyl-6-(3,5-di-t-butyl-4-hydroxybenzyl)-6-oxo-12H-dibenzo[d,g][1,3,2]dioxaphosphocin Using a 30 mm φ single-screw extruder, the above formulation was repelletized at 250° C. Using a laboplasto mill, the resulting pellets were kneaded at 240° C., 100 rpm under a nitrogen atmosphere. The time required for the torque value to become maximum (gel build-up time) was measured. The results are shown in Table 1. The longer the gel build-up time, the more the crosslinking on kneading is inhibited, which indicates excellent processing stability

TABLE 1

| | Example | | Comparative Example | | |
|---|---|---|---|---|---|
| | 1 | 2 | 1 | 2 | 3 |
| Test compound | C-1 | C-2 | — | P-1 | P-2 |
| Processing stability | 23.0 | 25.0 | 5.0 | 7.5 | 16.5 |

EXAMPLE 4

Heat Stability Test of Nylon

[Formulation]

| | |
|---|---|
| Unstabilized nylon 6 | 100 |
| Test compound | 0.5 |
| | (parts by weight) |

C-1: compound-1 (produced in Example 1)
P-1: 3,5-di-t-butyl-4-hydroxybenzylphosphonate-diethyl ester The above formulating materials were kneaded by dry blending and then kneaded at 300° C., 80 rpm for 5 minutes using a laboplasto mill. The torque value after 5 minutes is shown in Table 2. The higher the torque value after 5 minutes, the better the processing stability becomes because nylon 6 is decomposed by deterioration to reduce the torque value.

TABLE 2

| | Example | Comparative Example | |
|---|---|---|---|
| | 1 | 1 | 2 |
| Test compound | C-1 | — | P-1 |
| Torque value (kgf) | 56 | 22 | 35 |

What is claimed is:
1. A pentavalent phosphorus compound represented by the formula (I):

$$R^A \underset{O}{\overset{E\ O}{\diagdown P \diagup}} -O-F-R^B \quad (I)$$

wherein $R^A$ is
  a bisphenylene group, an alkylenebisphenylene group or a thiobisphenylene group, represented by the formula (II):

(II)

[structure showing two phenyl rings connected by X, with substituents $R^1$, $R^2$, $R^3$]

wherein $R^1$ and $R^2$ each independently represents a hydrogen atom, an alkyl group having 1 to 8 carbon atoms, a cycloalkyl group having 5 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, $R^3$ represents a hydrogen atom or an alkyl group having 1 to 8 carbon atoms, X represents a direct bond, a sulfur atom, an unsubstituted methylene group or a methylene group substituted with an alkyl having 1 to 8 carbon atoms or a cycloalkyl having 5 to 8 carbon atoms, or a propylene group represented by the formula (IV):

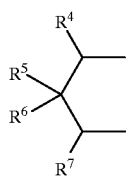

(IV)

wherein $R^4$, $R^5$, $R^6$ and $R^7$ each independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or an ethylene group represented by the formula (V):

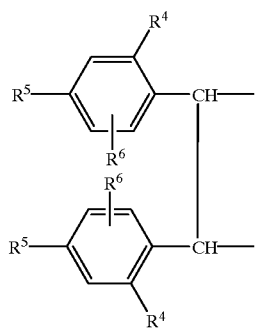

(V)

wherein $R^4$, $R^5$ and $R^6$ are as defined above,
E represents a direct bond or an oxygen atom,
F represents a connecting group, and
$R^B$ represents a group represented by the formula (XIV):

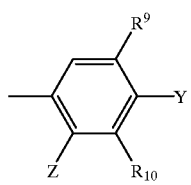

(XIV)

wherein $R^9$ represents an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, $R^{10}$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, Y represents a hydroxyl group, an alkoxy group having 1 to 8 carbon atoms or an aralkyloxy group having 7 to 12 carbon atoms, and Z represents a hydrogen atom, an alkyl group having 1–8 carbon atoms, a cycloalkyl group having 5 to 8 carbon atoms, an alkylcycloalkyl group having 6 to 12 carbon atoms, an aralkyl group having 7 to 12 carbon atoms, a phenyl group, a hydroxyl group, an alkoxy group having 1 to 8 carbon atoms or an aralkyloxy group having 7 to 12 carbon atoms, or a group represented by the formula (XV):

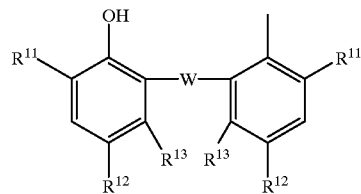

(XV)

wherein $R^{11}$ and $R^{12}$ each independently represent a hydrogen atom, an alkyl group having 1 to 8 carbon atoms, a cycloalkyl group having 5 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, and $R^{13}$ represents a hydrogen atom or an alkyl group having 1 to 8 carbon atoms, W represents a direct bond, a sulfur atom, an unsubstituted methylene group or a methylene group substituted with an alkyl group having 1 to 8 carbon atoms or a cycloalkyl group having 5 to 8 carbon atoms.

2. The pentavalent phosphorus compound according to claim 1 wherein F is a direct bond or a divalent connecting group having 1 to about 20 carbon atoms in total optionally having a hetero atom.

3. The pentavalent phosphorus compound according to claim 1 wherein F is represented by one of the following formulae (VI), (VII), (VIII), (IX), (X), (XI) and (XII):

| | |
|---|---|
| *—A— | (VI) |
| *—C(O)—A— | (VII) |
| *—B—O—A— | (VIII) |
| *—B—O—C(O)—A— | (IX) |
| *—D—C(O)—O—A— | (X) |
| *—G—N($R^8$)—A— | (XI) |
| *—G—N($R^8$)—C(O)—A— | (XII) | wherein *— represents a bond to the oxygen atom, A represents a direct bond or an alkylene group having 1 to 8 carbon atoms, B represents a divalent alcohol residue, D represents an alkylene group having 1 to 8 carbon atoms, G represents an alkylene group having 2 to 8 carbon atoms, and $R^8$ represents a hydrogen atom, an alkyl group having 1 to 8 carbon atoms or a group represented by the formula (XIII)

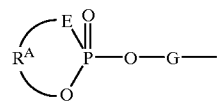

(XIII)

wherein $R^A$, E are as defined for Formula (I) and G is as defined above.

4. A method for stabilizing an organic material which comprises combining the pentavalent phosphorous compound according to claim 1 with an organic material.

5. The method according to claim 4, wherein the organic material is a thermoplastic resin.

6. The method according to claim 5, wherein the thermoplastic resin is a polyolefin or an engineering resin.

7. A composition which comprises the pentavalent phosphorous compound according to claim 1 and an organic material.

8. The composition according to claim 7, wherein the organic material is a thermoplastic resin.

9. The composition according to claim 8, wherein the thermoplastic resin is a polyolefin or an engineering resin.

* * * * *